United States Patent
Walse et al.

(10) Patent No.: US 10,011,580 B2
(45) Date of Patent: Jul. 3, 2018

(54) DIASTEREOSELECTIVE SYNTHESIS OF (±)-EPIANASTREPHIN, (±)-ANASTREPHIN AND ANALOGS THEREOF

(71) Applicant: The United States of America, as Represented by the Secretary of Agriculture, Washington, DC (US)

(72) Inventors: Spencer S. Walse, Fresno, CA (US); Daniel Kuzmich, Clovis, CA (US)

(73) Assignee: The United States of America, as Represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 15/492,340

(22) Filed: Apr. 20, 2017

(65) Prior Publication Data

US 2017/0305874 A1 Oct. 26, 2017

Related U.S. Application Data

(60) Provisional application No. 62/325,789, filed on Apr. 21, 2016.

(51) Int. Cl.
| | |
|---|---|
| *C07D 307/83* | (2006.01) |
| *C07C 45/66* | (2006.01) |
| *C07C 49/497* | (2006.01) |
| *C07C 51/04* | (2006.01) |
| *C07C 67/327* | (2006.01) |
| *C07C 69/732* | (2006.01) |
| *C07C 69/734* | (2006.01) |
| *C07C 51/09* | (2006.01) |

(52) U.S. Cl.
CPC .......... *C07D 307/83* (2013.01); *C07C 45/66* (2013.01); *C07C 49/497* (2013.01); *C07C 51/09* (2013.01); *C07C 67/327* (2013.01); *C07C 69/732* (2013.01); *C07C 69/734* (2013.01); *C07C 2601/14* (2017.05); *C07C 2601/16* (2017.05)

(58) Field of Classification Search
CPC ..... C07D 307/83; C07C 45/66; C07C 49/497; C07C 51/04; C07C 67/327; C07C 69/732; C07C 69/734
See application file for complete search history.

(56) References Cited

U.S. PATENT DOCUMENTS 8,128,948 B1 3/2012 Teal et al.

OTHER PUBLICATIONS

Battiste et al., 24(26) Tetrahedron Letts. 2611-14 (1983) (CAS Abstract) (Year: 1983).*

Arisawa, Meiko, et al.,"Equatorial Preference in the GaCl3-Promoted Ethenylation of Cyclic Ketones", Synthesis, (2002), No. 1, 138-145.
Battiste, Merle A. et al., "Anastrephin and Epianastrephin, Novel Lactone Components Isolated From the Sex Pheromone Blend of Male Caribbean and Mexican Fruit Flies1," (Tetrahedron Letters), (1983), 24(26): 2611-2614.
Bunce, Richard A., et al., Amberlyst-15 Promoted Synthesis of Fused and Spiro y-Butyrolactpones ffrom β-Hydroxyesters, Synthetic Communications, (1989), 19(13&14):2423-2430.
Fujita, Tsutomu et al., "Iodine Mediated Lactonization of Terpenic 3-Hydroxy Acids", Synthesisi, (2001), 12, 1846-1850.
Imamura, Paulo M., et al., "Chlorosulfonic Acid Mediated Cyclization of Homoterpenic Acid", Synthetics Communications, (1997), 27(14): 2479-2485.

(Continued)

*Primary Examiner* — Timothy R Rozof
(74) *Attorney, Agent, or Firm* — John D. Fado; G. Byron Stover

(57) ABSTRACT

A process for the synthesis of trans-fused γ-lactones having Formula (IV) from substituted cyclic ketones having Formula (I). A diastereoselective synthesis of (±)-epianastrephin (1) (wherein: $R^1$ is ethenyl, $R^2$ and $R^3$ is methyl, and n is 1), (±)-anastrephin (2) (wherein: $R^2$ is ethenyl, $R^1$ and $R^3$ is methyl and n is 1), and analogs thereof (wherein: $R^1$ is H, $C_{1-5}$ alkyl, $C_{2-6}$ alkenyl or $C_{2-6}$ alkynyl, $R^2$ is H, $C_{1-5}$ alkyl, $C_{2-6}$ alkenyl or $C_{2-6}$ alkynyl, $R^1$ and $R^2$ together with the carbon atom they are attached form a $C_{3-6}$ cycloalkyl ring, $R^3$ is $C_{1-5}$ alkyl and n is 0-2):

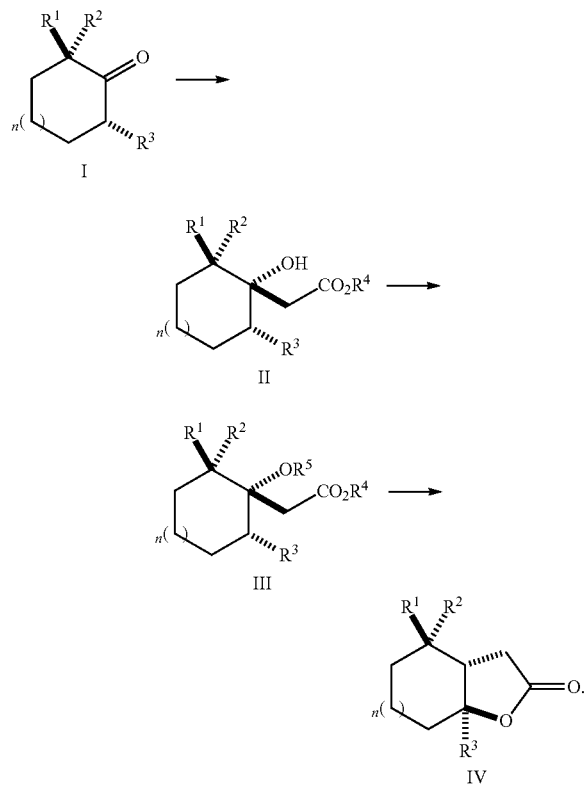

41 Claims, No Drawings

(56) References Cited

OTHER PUBLICATIONS

Jones, Ian L. et al., "Total Synthesis of (±)-Cordypyridones A and B and Related Epimers," Organic Letters, (2009), 11(23):5526-5529.
Matsumoto, TakAshi et al., "The Sterochemistry of Nucleophilic. Addition. IV.1) The Condensation of 2,2,6-Trimethylcyclohexanone With t-Butyl Acetate in the Presence of Lithium Amide", Bulletin of the Chemical Society of Japan, (1972), 45:1147-1152.
Rocca, James R. et al., "Comparison of Volatiles Emitted by Male Caribbean and Mexican Fruit Flies", Journal of Chemical Ecology, (1992), 18(2):223-244.
Saito, Akira A. et al., "Synthesis of (+)-Anastrephin and (+)-Epianastrephin", The Chemical Society of Japan (Chemistry Letters), (1984), pp. 729-730.
Wada, Kyohei et al., "Efficient Synthesis of Anastrephin Via the Allylic Substitution for Quaternary Carbon Construction", Georg Thieme Verlag Stuttgart, (2016), Synlett 27, A-E.
Black, T.H. et al. "cis-Fused γ-lactones from simple precursors via β-lactone rearrangements", Chemical Communication, vol. 8, pp. 753-754 (2001).
Walse, S.S. et al. "Glucosylated suspensosides, water-soluble pheromone conjugates from the oral secretions of male Anastrepha suspensa", Journal of Natural Products, vol. 71, pp. 1726-1731 (2008).
Kasashima, Y. et al. "Convenient preparative method for lactones from 3-hydroxy propanoic acids using iodine under solvent-free conditions", Journal of Oleo Science, vol. 56, No. 4, pp. 189-193 (2007).
International Searching Authority, PCT/US2017/028645 for The United States of America, as Represented by Secretary of Agriculture et al., International Filing Date Apr. 20, 2017, AG000216-PCT.

* cited by examiner

DIASTEREOSELECTIVE SYNTHESIS OF (±)-EPIANASTREPHIN, (±)-ANASTREPHIN AND ANALOGS THEREOF

REFERENCE TO RELATED APPLICATION

This application claims the benefit of U.S. Provisional Application No. 62/325,789, filed 21 Apr. 2016, which is incorporated herein by reference in its entirety.

FIELD OF THE INVENTION

The present invention relates generally to synthetic processes of making trans-fused γ-lactones. In particular, the invention relates to a process of making diastereotopically pure pheromones (±)-epianastrephin or (±)-anastrephin and analogs thereof.

BACKGROUND OF THE INVENTION

The trans-fused γ-lactones, epianastrephin (1) and anastrephin (2) (Scheme 1), are male-produced sex and aggregation pheromones of Caribbean (*Anastrepha suspensa*), Mexican (*Anastrepha ludens*), and South American (*Anastrepha fraterculus*) fruit flies (Nation, J. L., Ann. Entomol. Soc. Amer., 65: 1364 (1972); Nation, J. L., Environ. Entomol., 4: 27 (1975); Lima, I. S., et al., J. Braz. Chem. Soc., 12: 196 (2001)). In most agriculturally important regions of the United States, outbreaks of *A. suspensa* and *A. ludens* are regulated with quarantines to minimize potential damage of commercially valuable host fruit (USDA, APHIS, Fruit Fly Exclusion and Detection Programs 2011, Exotic Fruit Fly Strategic Plan FY2011-2015). Currently, trapping and monitoring devices rely on food-based lures, while a lure involving the epianastrephin (1) and anastrephin (2) pheromones is lacking because of insufficient synthetic routes to the quantities required for commercial-scale utilization (Tan, K. H., et al., Pheromones, male lures, and trapping of tephritid fruit flies; and Epsky, N. D., et al., History and development of food-based attractants, IN: Trapping and the detection, control, and regulation of tephritid fruit flies, Shelly, T., et al., Eds., Springer: Dordrecht, 2014, pp. 15-118).

Scheme 1

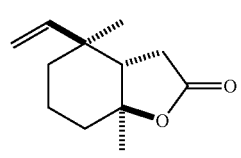

epianastrephin

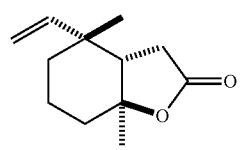

anastrephin

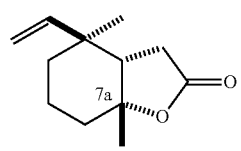

7a-epi-epianastrephin

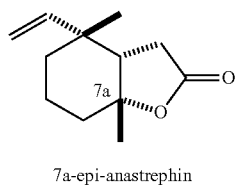

7a-epi-anastrephin

Pheromones 1 and 2 are naturally emitted from the oral secretions deposited by males to mark mating sites, and the mechanism of release provides insight toward their potential agricultural use as well as the importance of an efficient synthetic route toward this end. In addition to 1 and 2, oral secretions of males contain trans-fused γ-hydroxy acids 5a (hydrolysate 1→5a) and 5b (hydrolysate 2→5b), dehydration product 7 (derived from 5a or 5b), and glucoconjugate 8. All of these compounds are related through aqueous equilibrium that serves to abiotically release the relatively volatile lactones 1 and 2 over extended periods of time (Lu, F., and Teal, P. E. A., Arch. Insect Biochem. Physiol., 48: 144 (2001); Walse, S. S., et al., Green Chem. Lett. Rev., 1: 205 (2008); Walse, S. S., et al., U.S. Pat. No. 8,128,948, Compositions and Methods for Attracting *Anastrepha* Species, (June 2008)). Thus, an efficient synthesis of compounds 1 and 2 provides access to pheromone (1 and 2) as well as precursory forms 5a, 5b, 7, or 8 (or combinations thereof), all useful for the attraction of certain *Anastrepha* species (Scheme 2).

Scheme 2

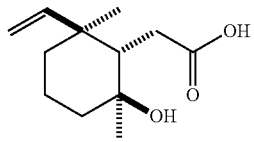

5a

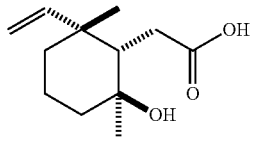

5b

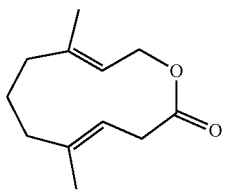

suspensolide

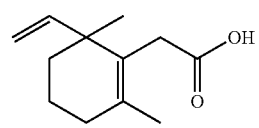

7

-continued

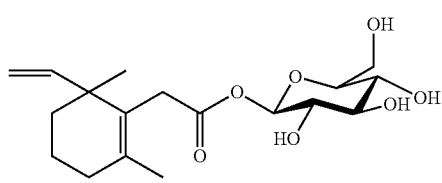

8

Several racemic and enantioselective syntheses of pheromones 1 and 2 are known (see, Battiste, M. A., et al., Tetrahedron Lett., 24: 2611 (1983); and references cited therein; for additional syntheses of anastrephin and epianastephin, see: Visnick, M., Ph.D. Dissertation, University of Florida, 1983; Strekowski, L., et al., J. Org. Chem., 51: 4836 (1986); Saito, A., et al., Chem. Lett. 729 (1984); for a synthesis of mixtures of 1 and 2 via an acid-catalyzed rearrangement of suspensolide (6), see: Battiste, M. A., et al., Tetrahedron Lett., 32: 5303 (1991); for biomimetic synthesis via suspensolide, see: Mori, K., et al., Ann. Chem., 167 (1988); Battiste, M. A., et al., Tetrahedron Lett., 29: 6565 (1988); Vecchio, G. H.-D., and Oehlschlager, A. C., J. Org. Chem., 59: 4853 (1994); Battiste, M. A., et al., J. Org. Chem., 61: 6454 (1996); for enantioselective syntheses of (−)-anastrephin, (−)-epianastrephin and (+)-epianastrephin, see: Wada, K., et al., Synlett., 27: A-E (2016); Tadano, K., et al., Tetrahedron Lett., 33: 7899 (1992); Tadano, K., et al., J. Org. Chem., 58: 6266 (1993); Irie, O., and Shishido, K., Chem. Lett., 53 (1995); Schultz, A. G., and Kirincich S. J., J. Org. Chem., 61: 5626 (1996); for access to trans-lactones via cyclization of the corresponding trans-fused γ-hydroxy acids 5a (condensation 5a→1) and 5b (condensation 5b→2), see: Strekowski, L., and Battiste, M. A., Tetrahedron Lett., 22: 279 (1981)). However, none of the aforementioned synthetic routes have satisfied the mass production requirements for formulation studies, field trials and commercialization (Nation, J. L., The role of pheromones in the mating system of *Anastrepha* fruit flies, IN: Fruit flies: their biology, natural enemies and control, Robinson A. S., and Hopper, G., Eds., Elsevier: Amsterdam, 1989, Vol. 3A, pp 189-205). A short and scalable process for the diastereoselective synthesis of compounds of formula (±)-1 and (±)-2, therefore, would be highly desirable (note that *A. suspensa* produces a nearly racemic mixture of both 1 and 2 (ee range 55±3 (−)/45±3 (+) with the 3aS,7aS-configuration assigned to the major (−) enantiomers), see Strekowski, L., et al., J. Org. Chem., 51: 4836 (1986); Saito, A., et al., Chem. Lett., 729 (1984); Battiste, M. A., et al., Tetrahedron Lett., 32: 5303 (1991); for the reported biological activity of enantiomers of 1 and 2, see: Robacker, D. C., and Hart, W. G., Entomol. Exp. Appl., 39: 103 (1985); Robacker, D. C., et al., Entomol. Exp. Appl., 40: 123 (1986)).

Under acidic conditions, trans-fused γ-lactones of Formula (IV) would not be expected from compounds of Formula (II) (where $R^4$ is H or $R^4$ is $C_{1-4}$ alkyl) (Scheme 3), as cis-fused γ-lactones formed with such catalysts as $H_2SO_4$ (Matsumoto, T., et al., Bull. Chem. Soc. Jpn., 45: 1147 (1972); Dobrev, A., and Ivanov, C., Synthesis, 8: 562 (1977); Watanabe, S., et al., J. Jpn. Oil Chem. Soc., 29: 43 (1980); Fujitga, T., et al., J. Org. Chem., 49: 1975 (1984)), amberlyst-15 resin (Bunce, R. A., et al., Synthetic Communications, 19: 2423 (1989)), and 12 (Fujita, T., et al., Synthesis, 12: 1846 (2001); Kasashima, Y., et al., J. Oleo Sci., 56: 189 (2007)). Further complicating these synthetic approaches, the acid-catalyzed isomerization of trans-fused γ-lactones of Formula (IV) to the thermodynamically more stable cis-fused γ-lactones readily occurs (Siato, A., et al., Chem. Lett., 1065 (1978); Hoye, T. R., and Kurth, M. J., J. Org. Chem., 43: 3693 (1978); Imamura, P. M., and Santiago, G. M. P., Synthetic Communications, 27: 2479 (1997)).

Similarly, under acid-conditions, we have observed the favored formation of cis-fused γ-lactones relative to trans-fused and the isomerization of the trans-fused γ-lactones to cis-fused. β-hydroxy ester of Formula (II) (where $R^1$ is ethenyl, $R^2$ is methyl, $R^3$ is methyl, and $R^4$ is t-butyl) was treated with catalytic $I_2$ at 80° C. for 4 h in $CH_3CN$ to yield hydrolysis of the t-butyl ester and cyclization to afford a 10:3:1 mixture, respectively, of cis- and trans-fused γ-lactones 3, 1 and 4 as determined by $^1H$ NMR (see, for the iodine-mediated hydrolysis of t-butyl esters, Yadav J. S., et al., Tetrahedron Lett., 47: 4921 (2006)) and lactonization (Fujita, T., et al., Synthesis, 1846 (2001)). Moreover, trans-fused γ-lactones 1 and 2 each isomerized to cis-fused γ-lactones 3 and 4 after treatment with $BF_3.Et_2O$ in acetonitrile at room temperature for 24 h. Treatment of trans-fused γ-lactone 1 with 1 N aqueous HCl at 80° C. for 3 h gave predominately cis-fused γ-lactone 3 and trace amounts (<5%) of γ-lactone 4.

Consequently, the prior-art references as well as our preliminary experimentation teach away from our invention and indicate that the use of acidic conditions to form trans-fused γ-lactones of Formula (IV), in large excess relative to cis-fused analogs, from intermediates of Formula (II) (where $R^1$, $R^2$, $R^3$, and $R^4$ have the meanings of, for example, n, $R^1$, $R^2$, $R^3$ and $R^4$ in the Summary of the Invention section) would be high risk, non-obvious, and surprising.

SUMMARY OF THE INVENTION

The present invention provides a synthetic process for making trans-fused γ-lactones of Formula (IV) starting from appropriately substituted cyclic ketones of Formula (I) and proceeding through intermediates of Formula (II) and then Formula (III) (where $R^5$ is acetyl). The process is suitable for the diastereomerically pure synthesis of compound of Formula (IV) when $R^1$ does not equal $R^2$ (such as in the preparation of trans-fused γ-lactones 1 or 2). In all schemes, unless specified otherwise, n, $R^1$, $R^2$, $R^3$, $R^4$ and $R^5$ in the formulas in Scheme 3 have the meanings of n, $R^1$, $R^2$, $R^3$, $R^4$ and $R^5$ in the Summary of the Invention section.

Scheme 3

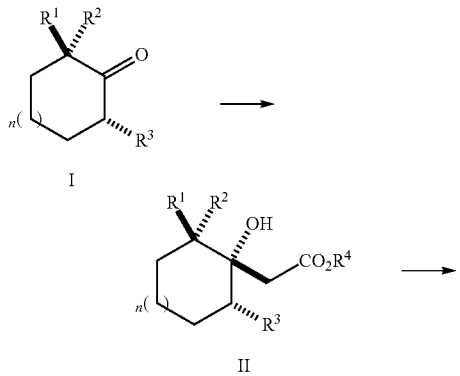

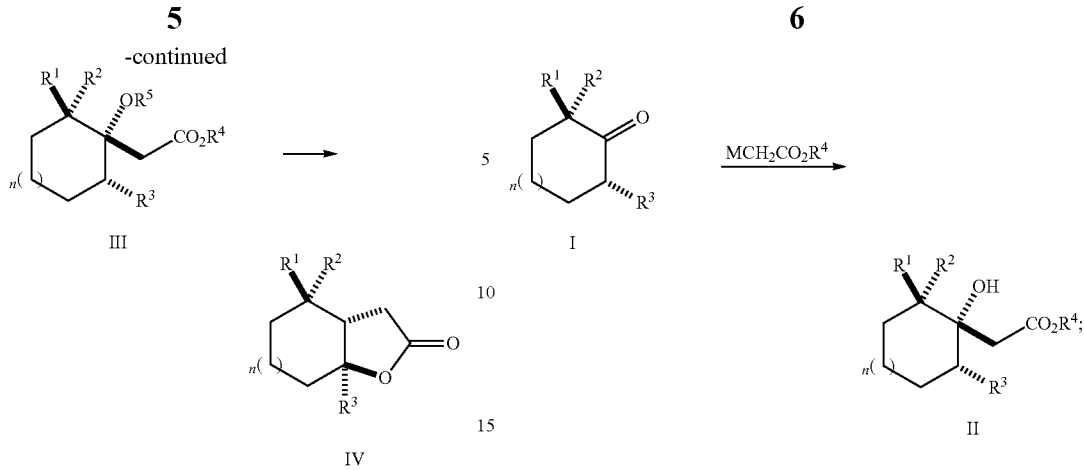

In the broadest generic aspect the invention relates to a synthetic process for the preparation of trans-fused γ-lactones of the Formula (IV)

$$\text{(IV)}$$

wherein:
$R^1$ is H, $C_{1-5}$ alkyl, $C_{2-6}$ alkenyl or $C_{2-6}$ alkynyl,
$R^2$ is H, $C_{1-5}$ alkyl, $C_{2-6}$ alkenyl or $C_{2-6}$ alkynyl,
$R^1$ and $R^2$ together with the carbon atom to which they are attached form a $C_{3-6}$ cycloalkyl ring,
$R^3$ is $C_{1-5}$ alkyl,
n is 0, 1, or 2 to form a 5-, 6- or 7-membered ring.

Another embodiment of the invention provides for the diastereoselective synthesis of compounds of the Formula (IV), wherein:
$R^1$ is H, $C_{1-5}$ alkyl, $C_{2-6}$ alkenyl or $C_{2-6}$ alkynyl,
$R^2$ is H, $C_{1-5}$ alkyl, $C_{2-6}$ alkenyl or $C_{2-6}$ alkynyl,
$R^1$ and $R^2$ are not equal,
$R^3$ is $C_{1-5}$ alkyl,
n is 0, 1, or 2 to form a 5-, 6- or 7-membered ring.

In yet another aspect of the invention, preferred embodiment provides for the diastereoselective synthesis of (±)-epianastrephin (1) and (±)-anastrephin (2) of the Formula (IV), wherein:
$R^1$ or $R^2$ is methyl or ethenyl,
$R^1$ and $R^2$ are not equal,
$R^3$ is methyl,
n is 1 to form a 6-membered ring.

In the broadest sense we disclose herein processes for the synthesis of compound of Formula (IV) containing various $R^1$, $R^2$ and $R^3$ groups and n is 0, 1, or 2 the process comprising:

(a) forming the β-hydroxy ester of Formula (II) by reacting, in a suitable solvent, the ketone of Formula (I) with an organometallic reagent $MCH_2CO_2R^4$ where M is Li, Na, K, or MgX (where X is Cl, Br, or I), and $R^4$ is $C_{1-4}$ alkyl (b) reacting the alcohol of Formula (II) with an acylating agent (such as acetyl chloride or acetic anhydride), or a chloroformate (such as ethyl chloroformate) in the presence of a suitable catalyst or a suitable base in a suitable solvent, or an acyl transfer reagent in the presence of an acid catalyst and organic catalyst in a suitable solvent to provide the alcohol of Formula (III) where $R^5$ is —C(O)$C_{1-6}$ alkyl or —C(O)O$C_{1-6}$ alkyl

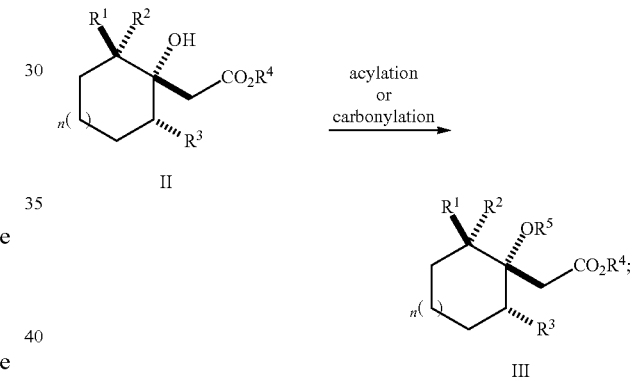

(c) cyclizing the compound of Formula (III) with a suitable organic acid or a Lewis acid in a suitable solvent to form the trans-fused γ-lactone of Formula (IV)

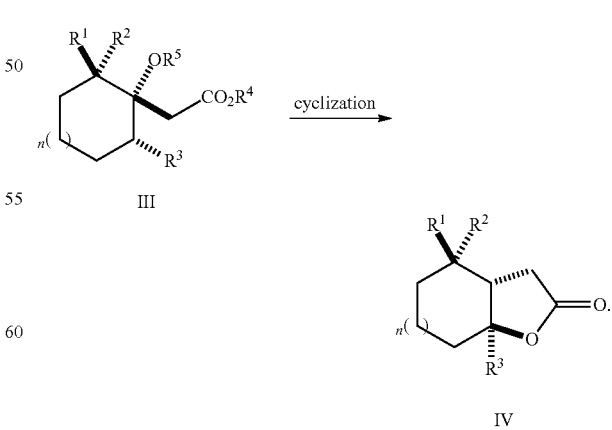

In an aspect of the invention, the suitable solvent of step (a) is tetrahydrofuran (THF), diethyl ether, tert-butyl methyl ether (MTBE), ethylene glycol dimethyl ether (DME), dioxane, or a mixture thereof, preferably THF.

In an aspect of the invention, the organometallic reagent (MCH$_2$CO$_2$R$^4$ where M is Li, Na, K of step (a) is generated from (1) the corresponding neutral acetate precursor with a base selected from lithium diisopropylamide (LDA) or lithium bis(trimethylsilyl)amide (LiHMDS), sodium hexamethyldisilazide (NaHMDS), potassium hexamethyldisilazide (KHMDS), sodium hydride, potassium hydride or from (2) the Grignard reagent generated from the corresponding α-halo ester (XCH$_2$CO$_2$R$^4$ where X is Cl, Br, or I) and isopropyl magnesium bromide or magnesium. Regarding (1), treatment of esters with a suitable base can lead to the formation of a nucleophilic species called an enolate that will react with an electrophile. These C nucleophiles are useful for making new carbon-carbon bonds. Regarding (2), typical Grignard reactions involve the use of a magnesium ribbon. Magnesium is coated with a passivating layer of magnesium oxide which inhibits reactions with the organic halide. Specially activated magnesium, such as Rieke magnesium, circumvents this problem (Arisawa, M., et al., Synthesis, 34: 138 (2002)). The oxide layer can also be broken up using ultrasound (Cazeua, P., et al., J. Tetrahedron, 43: 2075 (1987)) or by adding a few drops of iodine or 1,2-diiodoethane. Or Mg transfer reaction (halogen-Mg exchange) can be used. An alternative preparation of Grignard reagents involves transfer of Mg from a preformed Grignard reagent to an organic halide. This method offers the advantage that the Mg transfer tolerates many functional groups. A typical reaction involves isopropylmagnesium chloride and aryl bromide or iodides (Tashiro, D., et al., J. Org. Chem., 62: 8141 (1997)).

In an aspect of the invention, the suitable solvent of step (b) is dichloromethane (DCM), acetonitrile, nitromethane, or a mixture thereof, preferably acetonitrile.

In an aspect of the invention, the suitable catalyst of step (b) is indium (III) chloride (Chakraborti, A. K., et al., Tetrahedron Lett., 44: 6749 (2003)), lithium trifluoromethanesulfonate (LiOTf) (Karimi, B., Maleki, J. J. Org. Chem., 68: 4951 (2003)) or N-bromosuccinimide (NBS).

In an aspect of the invention, the suitable organic base of step (b) is triethylamine (TEA) or Hunig's base.

In an aspect of the invention, the suitable acyl transfer reagent of step (b) is isopropenyl acetate, vinyl acetate or methyl vinyl acetate, preferably isopropenyl acetate In an aspect of the invention, the suitable acid catalyst of step (b) is para-toluenesulfonic acid monohydrate (p-TsOH.H$_2$O) or methane sulfonic acid, preferably p-TsOH.H$_2$O.

In an aspect of the invention, the suitable acyl transfer organic catalyst of step (b) is an oxime, preferably cyclohexanone oxime.

In another aspect of the invention suitable organic acid of step (c) is p-TsOH.H$_2$O, MeSO$_3$H and a suitable Lewis acid complex of step (c) is BX$_3$.L, GaX$_3$.L, or AlX$_3$ where X is F, Cl or Br, and where L is diethyl ether (Et$_2$O) or acetonitrile or dimethyl sulfide, preferably p-TsOH.H$_2$O or BF$_3$.Et$_2$O.

In another aspect of the invention a suitable solvent of step (c) is acetonitrile or nitromethane, preferably acetonitrile.

Another aspect of the invention is directed toward the diastereoselective synthesis of (±)-epianastrephin (1):

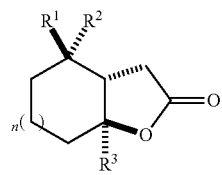

a compound of Formula (IV):

wherein:

R$^1$ is ethenyl,

R$^2$ is methyl,

R$^3$ is methyl, and n is 1 to form a 6-membered ring, the process comprising:

(a) reacting ketone 9 with a suitable base (such as LDA or LiHMDS) followed by zinc chloride and acetaldehyde in a suitable solvent (such as THF) to form alcohol 10

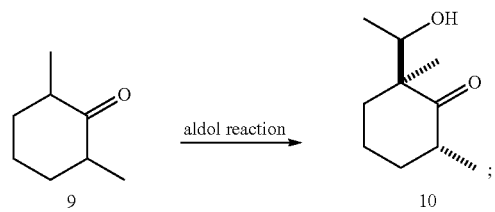

(b) reacting alcohol 10 with a dehydrating agent in a suitable solvent (such as toluene, pyridine or DCM) to form vinyl ketone 11, or reacting the alcohol 10 with a sulfonyl chloride (such as methanesulfonyl chloride or p-toluenesulfonyl chloride (p-TsCl)) in a suitable solvent followed by elimination with a suitable base (such as 2,4,6-trimethylpyridine or 1,8-diazabicyclo[5.4.0]undec-7ene) to form vinyl ketone 11

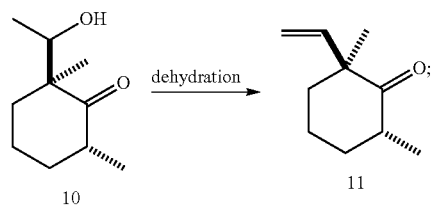

(c) reacting vinyl ketone 11 with an organometallic reagent MCH$_2$CO$_2$R$^4$ where M is Li, Na, K, or MgX, where X is Cl, Br, or I, where R$^4$ is C$_{1-4}$ alkyl, preferably R$^4$ is t-butyl, in a suitable solvent to form alcohols 12A and 12B

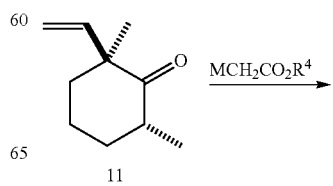

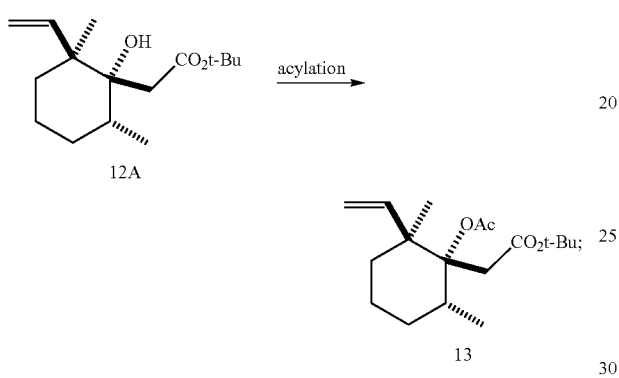

(d) reacting alcohol 12A with an acylating agent (such as isopropenyl acetate) in the presence of an acid catalyst (such as p-TsOH.H$_2$O) and cyclohexanone oxime in a suitable solvent to provide the acylated alcohol 13

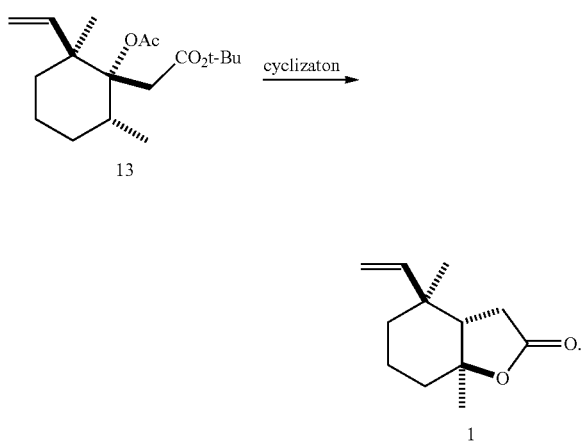

(e) cyclizing compound 13 with a suitable Lewis acid complex (such as BX$_3$.L, GaX$_3$.L, or AlX$_3$ where X is F, Cl or Br, and where L is Et$_2$O, acetonitrile or dimethyl sulfide), preferably BF$_3$.Et$_2$O in a suitable solvent (such as acetonitrile) to form, diastereoselectively, the trans-fused γ-lactone, epianastrephin (1)

In an aspect of the invention, the suitable dehydrating agent of step (b) is bis[α,α-bis(trifluoromethyl)benzenemethanolato]diphenylsulfur (Martin's sulfurane), Burgess's reagent, P$_2$O$_5$, or SOCl$_2$, preferably Martin's sulfurane.

Another aspect of the invention is also directed toward the diastereoselective synthesis of (±)-anastrephin (2):

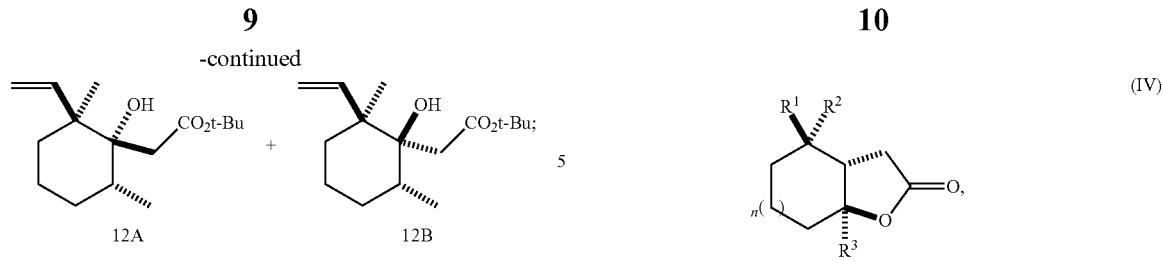

a compound of Formula (IV):

wherein:

$R^1$ is methyl, $R^2$ is ethenyl, $R^3$ is methyl, and n is 1 to form a 6-membered ring, the process comprising:

(a) reacting ketone 9 with a silyl chloride (such as chlorotrimethylsilane (TMSCl)), a suitable base (such as TEA) and sodium iodine in a suitable solvent (such as acetonitrile); or reacting ketone 9 with a base (such as LDA, NaHMDS or LHMDS) and a silyl chloride (such as TMSCl) in a suitable solvent (such as THF) to form silyl enol ether 14

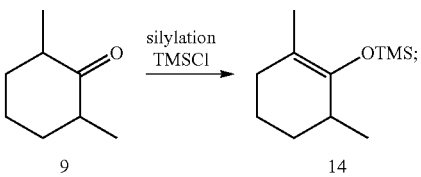

(b) reacting silyl enol ether 14 with ethynyltrimethylsilane (TMSA) in the presence of a Lewis acid (such as GaCl$_3$) in a suitable solvent (such as pentane or methylcyclohexane) followed by the addition of THF and a suitable acid (such as sulfuric acid) to form ketone 15

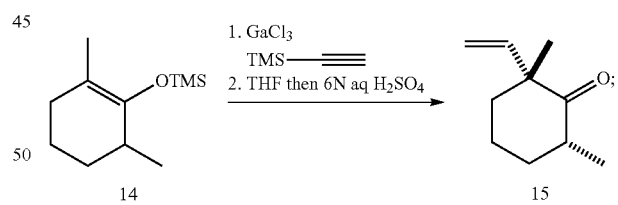

(c) reacting ketone 15 with an organometallic reagent MCH$_2$CO$_2$R$^4$ where M is Li, Na, K, or MgX, where X is Cl, Br, or I, where R$^4$ is C$_{1-4}$ alkyl, preferably R$^4$ is t-butyl, in a suitable solvent to form alcohols 16A and 16B

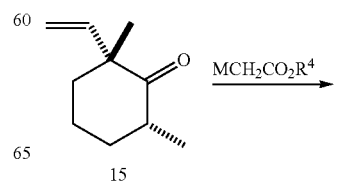

-continued

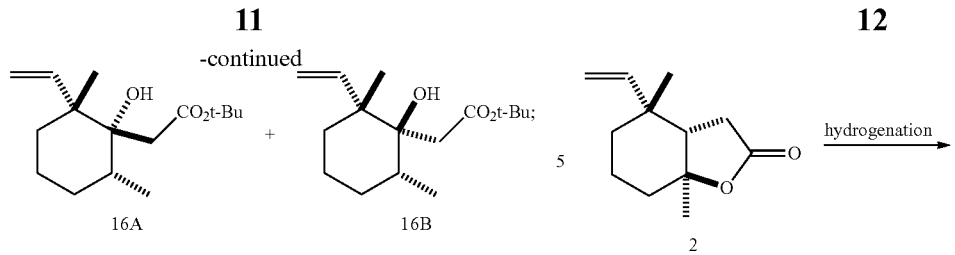

(d) reacting alcohol 16A with an acyl transfer reagent (such as isopropenyl acetate) in the presence of an acid catalyst (such as p-TsOH.H₂O) and cyclohexanone oxime in a suitable solvent to provide acylated alcohol 17

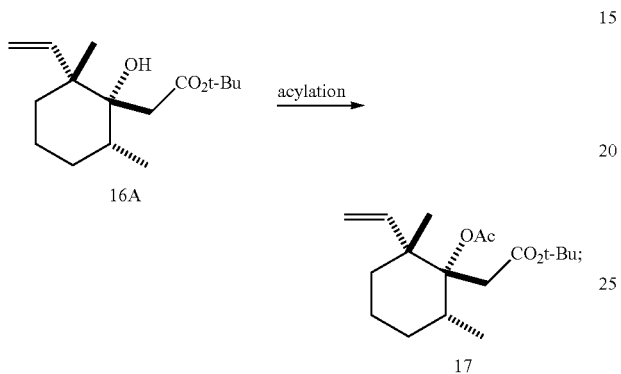

(e) cyclizing compound 17 with a suitable Lewis acid or Lewis acid complex (such as BX₃.L, GaX₃.L, or AlX₃ where X is F, Cl or Br and L is Et₂O or acetonitrile or dimethyl sulfide), in a suitable solvent (such as acetonitrile) to form, diastereoselectively, the trans-fused γ-lactone, anastrephin (2)

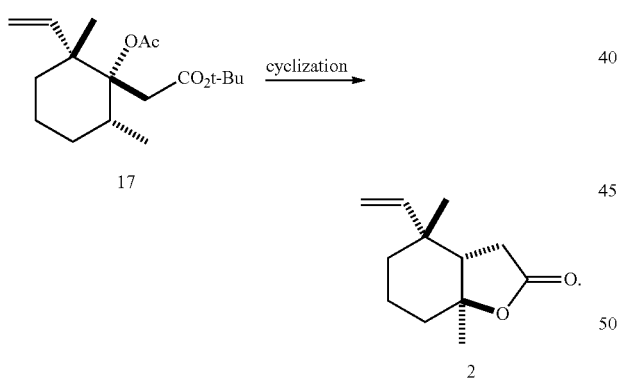

Yet another approach to compounds of Formula (IV) where various R¹ and R² are C₂₋₅ alkyl comprises the reduction of compounds of Formula (IV) where R¹ is C₂₋₆ alkenyl or C₂₋₆ alkynyl, R² is C₂₋₆ alkenyl or C₂₋₆ alkynyl, the process by example comprising of Formula (IV) (wherein: n is 1, R¹ is ethenyl, R² is methyl and R³ is methyl):

(a) hydrogenation of (±)-anastrephin (2) using a suitable catalyst (such as 10% palladium on carbon, Adam's catalyst, Lindlar's catalyst, palladium (II) sulfide or palladium on barium sulfate) in a suitable solvent such as (methanol, ethanol, ethyl acetate or a mixture thereof), preferably ethyl acetate, to form compound 18

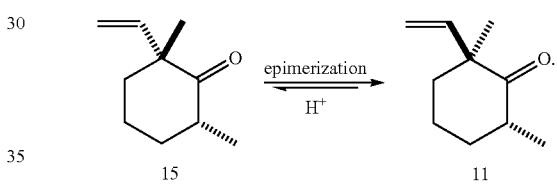

Yet another approach to ketone 11 and the process towards the synthesis of compounds of Formula (IV) where n is 1, R¹ is ethenyl, R² is methyl and R³ is methyl:

(a) isomerization of ketone 15 using a suitable acid catalyst (such asp-TsOH.H₂O, trifluoroacetic acid, sulfuric acid) in a suitable solvent (such as toluene or DCM); or isomerization of ketone 15 using a suitable base (such as LDA, NaH or KH) in a suitable solvent (such as THF, dioxane or DME) followed by protonation to provide the diastereomeric ketone 11

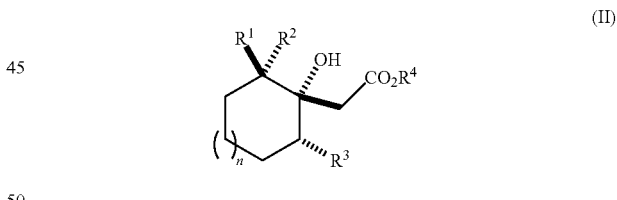

Another aspect of the invention is directed toward the synthesis of the aglycon 7 of suspensosides A and B (8) from a compound of Formula (II)

$$\text{(II)}$$

wherein:
R¹ is ethenyl or methyl,
R² is ethenyl or methyl,
R¹ and R² are not the same,
R³ is methyl,
R⁴ is C₁₋₄ alkyl, and
n is 1 to form a 6-membered ring
the process by example comprising of Formula (II) (wherein: n is 1, R¹ is methyl, R² is ethenyl, R³ is methyl, and R⁴ is 1-butyl):

(a) dehydrating alcohol 12A with a suitable dehydrating agent in a suitable solvent to provide the olefin 19, or reacting alcohol 12A with a sulfonyl chloride (such as methanesulfonyl chloride or p-TsCl) in a suitable solvent followed by elimination with a suitable base (such as 2,4,6-trimethylpyridine or 1,8-diazabicyclo[5.4.0]undec-7ene) to provide olefin 19

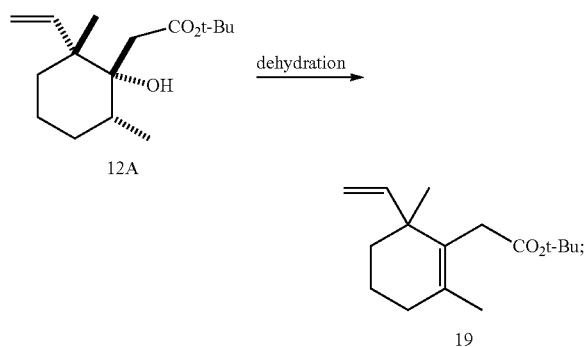

12A

19

(b) deprotection of the t-butyl ester of olefin 19 with a suitable acid (such as p-TsOH.H$_2$O) in a suitable solvent (such as CH$_3$CN) to provide the aglycon 7 of suspensosides A and B (8)

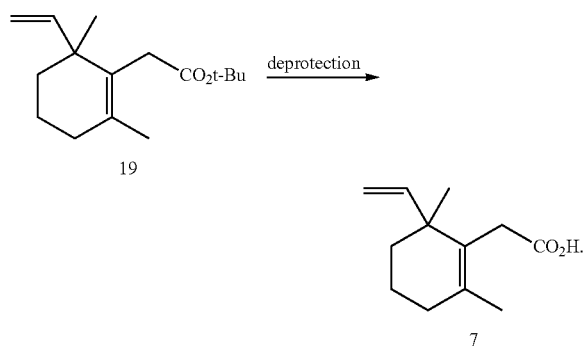

19

7

In an aspect of the invention, the suitable dehydrating agent of step (a) is SOCl$_2$, bis[α,α-bis(trifluoromethyl) benzenemethanolato]diphenylsulfur (Martin's sulfurane), Burgess's reagent, or P$_2$O$_5$, preferably SOCl$_2$.

In an aspect of the invention, the suitable solvent of step (a) is pyridine, toluene, or DCM, preferably pyridine.

In another embodiment of the invention there is provided various compounds of Formula (II), Formula (III) and intermediates useful for compounds of Formula (IV) as provided in Table 1 that constitute part of the invention and the process for making (±)-epianastrephin (1) and (±)-anastrephin (2) and analogs thereof. The compounds of Table 1 can be made according to the general schemes and specific examples. The stereochemistry of compounds in Table 1 are in the relative sense only.

Isomers are defined as diastereomers or enantiomers. Each stereocenter maybe in the R or S configuration or a combination of configurations. All isomeric forms of the compounds of Formula (I), (II) and (III) are included in the invention and in the process of making compounds of Formula (IV) (i.e., (±)-epianastrephin (1), (±)-anastrephin (2) as well as analogs thereof).

This summary is provided to introduce a selection of concepts in a simplified form that are further described below in the detailed description. This summary is not intended to identify key features or essential features of the claimed subject matter, nor is it intended as an aid in determining the scope of the claimed subject matter.

DETAILED DESCRIPTION OF THE INVENTION

In the broadest sense the invention is directed toward a process for the synthesis of trans-fused γ-lactones of Formula (IV) containing various R$^1$, R$^2$ and R$^3$ groups, in general, the diastereoselective synthesis of the insect pheromones (±)-epianastrephin (1), (±)-anastrephin (2), as well as analogs thereof, exemplify the process.

Herein we disclose novel processes for making gram-scale quantities of (±)-epianastrephin (1), or (±)-anastrephin (2), and analogs thereof. Currently, there are no commercial formulations using (±)-epianastrephin and (±)-anastrephin (or any other pheromone) as attractants for control of *Anastrepha* sp., due, in large part, to a lack of a practical and efficient synthetic method suitable for gram-scale production. Compared to existing synthetic methodology for (±)-epianastrephin (1) and (±)-anastrephin (2), surprisingly our disclosure (i) affords diastereomerically pure (±)-epianastrephin and (±)-anastrephin, (ii) is suitable for gram-scale production, (iii) alleviates the need for tedious chromatographic separations of mixtures of (±)-epianastrephin (1) and (±)-anastrephin (2) (and such chromatographic separations are generally not utilized in the processes described herein), and (iv) is useful in the preparation of analogs of (±)-epianastrephin (1) and (±)-anastrephin (2) (i.e., compound 24(3aS*,7aS*)-2-Oxo-4,4,7a-trimethyloctahydrobenzofuran).

General Synthetic Methods: The present invention also discloses the diastereoselective synthesis of compounds of Formula (III), where R$^5$ is acetyl and R$^4$ is t-butyl, which are key intermediates in the synthesis of diastereoselective pure compounds of Formula (IV) (when R$^1$ does not equal R$^2$). Compounds of Formula (III) are prepared by modified general methods known to those skilled in the art (see, Rezaei, H., and Normant, J. F., Synthesis 2000, p. 109; Matsumoto, T., et al., Bull. Chem. Soc. Jpn., 45: 1147 (1972); and Curini, M., et al., J. Org. Chem., 55: 311 (1990); for the use of cyclohexanone oxime as a catalyst in the acetylation of tertiary alcohols under neutral conditions see, Tashiro, D., et al., J. Org. Chem., 62: 8141 (1997)). Intermediates of Formula (II) may be prepared from the corresponding cyclic ketone of Formula (I) according to known or general procedures, or prepared by one skilled in the art (e.g., Matsumoto, T., et al., Bull. Chem. Soc. Jpn., 45: 1147 (1972) and Wada, A., et al., Synthesis, 37: 1581 (2005)). Substituted cyclic ketones of Formula (I) are either commercially available, prepared according to known or general procedures described below, or prepared by one skilled in the art using methods described in the literature. For example compounds of Formula (I) (where R$^1$ is ethenyl, R$^2$ is methyl, R$^3$ is methyl and n is 1 or where R$^1$ is methyl, R$^2$ is ethenyl, R$^3$ is methyl and n is 1) are prepared according to known methods (e.g., Clive, D. L. J., et al., J. Org. Chem., 47: 1632 (1982) and Arisawa, M., et al., Synthesis, 34: 138 (2002)). Vinyl cyclohexanones of Formula (I) may also be prepared by general methods known to those skilled in the art (e.g., Jones, I. L., et al., Org. Lett., 11: 5526 (2009); Paterson, I., Tetrahedron, 44: 4207 (1988); and Chang, T. C. T., Organic Synthesis, 66: 95 (1988)). 2,2,6-Dimethylcyclohexanone can be prepared according to known methods; for example, Jung, M. E., Murakami, M., Org. Lett., 8: 5857 (2006). Novel synthetic intermediates useful in the synthesis of compounds of Formula (IV), prepared by general methods and exemplified below, also constitute part of the invention.

Definition of Terms and Conventions Used. Unless defined otherwise, all technical and scientific terms used herein have the same meaning as commonly understood by one of ordinary skill in the art to which the invention belongs. Other more specific definitions are as follows:

The terms "alkyl" or "alkyl group" mean a branched or straight-chain saturated aliphatic hydrocarbon monovalent radical. This term is exemplified by groups such as methyl, ethyl, n-propyl, 1,1-dimethylethyl (t-butyl or tert-butyl), and the like.

The terms "alkenyl" or "alkenyl group" mean a branched or straight-chain saturated aliphatic hydrocarbon monovalent radical containing at least one carbon-carbon double bond. This term is exemplified by groups such as ethenyl, propenyl, isopropenyl, and the like.

The terms "ethenyl" and "vinyl" have the same meaning.

The terms "alkynyl" or "alkynyl group" mean a branched or straight-chain saturated aliphatic hydrocarbon monovalent radical containing at least one carbon-carbon triple bond. This term is exemplified by groups such as ethynyl, propynyl, and the like.

The terms "cycloalkyl" or "cycloalkyl group" mean a non-aromatic saturated aliphatic ring of 3-6 carbon atoms. This term is exemplified by groups such as cyclopropyl, cyclobutyl, cyclopentyl, and the like.

The term "acyl" shall be understood to be a $C_{1-n}$alkyl with a carbonyl group wherein the point of attachment is via the carbonyl, for example: acetyl (—C(O)CH$_3$)

The terms "acylating agent" or "acyl transfer reagent" mean a compound that provide an acyl or acetyl group. This term is exemplified by a compound selected from acetyl chloride, acetic anhydride, isopropenyl acetate, vinyl acetate, methyl vinyl acetate, and the like.

The terms "halogen" or "halo" shall be understood to mean bromine, chlorine or iodine.

In the event that the structures of compounds disclosed here are in conflict with the nomenclature the compounds are defined by the structure.

The yield of each of the reactions described herein is expressed as a percentage of the theoretical yield.

Compounds of the invention also include their isotopically-labelled forms. Deuterium labelled compounds of Formula (IV) can be prepared according to known methods using commercially available deuterium labelled reagents (Arisawa, M., et al., Synthesis, 34: 138 (2002)).

Optimum reaction conditions, which may include the stoichiometry of reactants and reaction times, may vary depending on the particular reactants used. Unless otherwise specified, reagents, solvents, temperatures, and other reaction conditions may be readily selected by one of ordinary skill in the art.

Amounts and ranges are not meant to be limiting, and increments between the recited percentages and ranges are specifically envisioned as part of the invention. All ranges and parameters disclosed herein are understood to encompass any and all subranges subsumed therein, and every number between the endpoints. For example, a stated range of "1 to 10" should be considered to include any and all subranges between (and inclusive of) the minimum value of 1 and the maximum value of 10 including all integer values and decimal values; that is, all subranges beginning with a minimum value of 1 or more, (e.g., 1 to 6.1), and ending with a maximum value of 10 or less, (e.g. 2.3 to 9.4, 3 to 8, 4 to 7), and finally to each number 1, 2, 3, 4, 5, 6, 7, 8, 9, and 10 contained within the range.

Although any methods and materials similar or equivalent to those described herein can be used in the practice or testing of the present invention, the preferred methods and materials are now described.

The following examples are intended only to further illustrate the invention and are not intended to limit the scope of the invention as defined by the claims.

SYNTHETIC EXAMPLES

The following are representative examples that illustrate the process of the invention. Reactions requiring an inert atmosphere were run under nitrogen in commercially available (Aldrich) dry solvents unless noted otherwise. GaCl$_3$, isopropenyl acetate, t-butyl acetate, LDA, and LiHMSD were purchased from Aldrich Chemical. TMSA was purchased from Oakwood Chemical. Typically, reaction monitoring was performed by thin-layer chromatography on Analtech or E-Merck silica gel TLC plates or by gas chromatography-electron impact mass spectrometry (GC-EIMS). Developed plates were visualized using phosphomolybdic acid (PMA) stain. Typically, intermediates and products were purified by flash chromatography using 230-400 mesh Merck silica gel or pre-packed silica gel cartridges from Silicycle or by recrystallization. Melting points were recorded on a Mel-Temp II® and are uncorrected. Infrared spectra were recorded on a Nicolet iS10 Fourier Transform Infrared Spectrometer. Samples were analyzed as films applied to the instrument in volatile solvents and are reported as wavenumber (cm$^{-1}$). $^1$H and $^{13}$C NMR spectra were recorded on a Bruker Fourier 300 NMR spectrometer. Chemical shifts (δ) are reported as the shift in parts per million (ppm) from internal deuterated solvent, CDCl$_3$ at 7.26 and MeOD$_4$ at 3.31 ppm for proton and 77.16 and 49.00 ppm for carbon, respectively. $^1$H spectra data are reported as follows: chemical shift, number of protons, multiplicity ((s) singlet, (d) doublet, (t) triplet, (q) quartet, (qu) quintet, (m) multiplet), (b) broad, D$_2$O exchangeable, coupling constants (J) in hertz. Carbon spectral data are reported as follows: chemical shift (δ) and assignment (multiplicity determined using DEPT experiments). Mass spectra were recorded on a 7890A gas chromatograph and a 5975C quadrupole mass spectrometer or a 6890 gas chromatograph and a 5973N quadrupole mass spectrometer (Agilent Technologies, Santa Clara, Calif.) operated with electron impact (EI) ionization (70 eV). Cool on-column injections (~1 μL) were at 143° C. with He carrier gas (1.0 mL min$^{-1}$). The oven program methods were optimized for the compounds of interest (for example, Method A, useful for separation of compounds 1 through 4, was as follows: isothermal at 140° C. for 1 min, heated at 4° C. min$^{-1}$ to 150° C., isothermal for 70 min, heated at 30° C. min$^{-1}$ to 230° C., and then isothermal for 2 min; or (Method B), was as follows: isothermal at 60° C. for 1 min, heated at 10° C. min$^{-1}$ to 240° C., isothermal for 11 min. GlassSeal connectors (Supleco®, Milwaukee, Wis.) fused four columns in series; a deactivated column (L=8 cm, ID=0.53 mm) (Agilent Technologies, Santa Clara, Calif.: No. 160-2535-10) onto which the injection was deposited, a deactivated retention-gap column (L=2 m, ID=0.25 mm) (Agilent Technologies, Santa Clara, Calif.: No. 160-2255-30), a DB-1701 analytical column (L=60 m, ID=0.25 mm, df=0.25 μm) (J&W Santa Clara, Calif.: part #122-0762), and finally a deactivated column (L=1.5 m, ID=0.25 mm) (Agilent Technologies, Santa Clara, Calif.: No. 160-2255-30) that was directed into the detector. Transfer-line, source, and quadrapole temperatures were respectively 280, 230, and 150° C. Full scan spectra (m/z 50 to 600) with ±0.3 m/z resolution were acquired at 0.34 s per scan for qualitative verification. Mass spectral data are reported as mass-to-charge ratios (m/z) and relative intensity (% of base peak). All stereochemical depictions are in the relative sense.

The diastereoselective synthesis of a single diastereomer is carried out as exemplified below.

Example 1

Synthesis of (±)-epianastrephin (1)

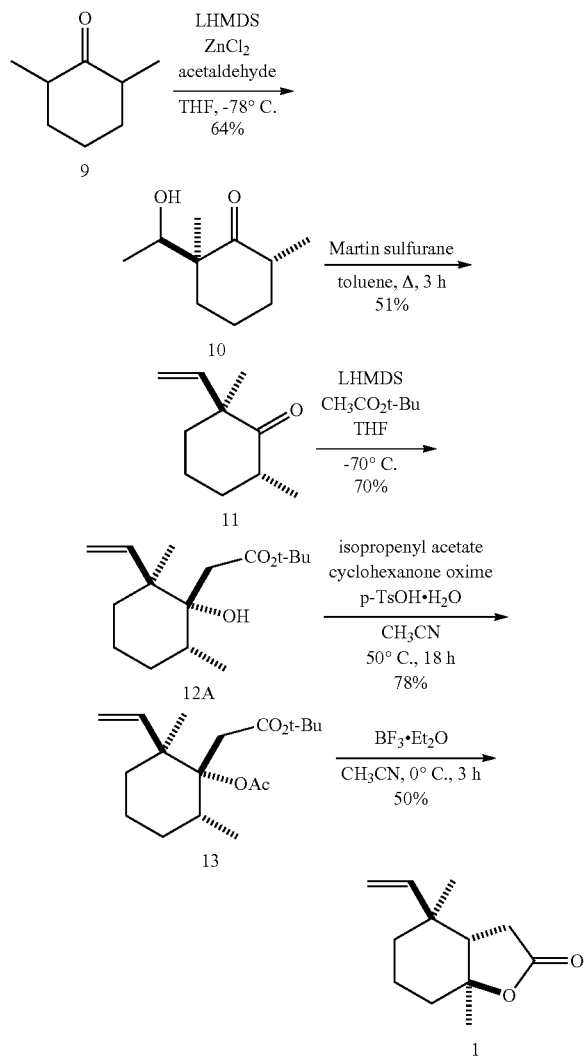

2-(1-Hydroxyethyl)-2,6-dimethylcyclohexanone (10): To a chilled (−78° C.) solution of 9 (12.6 g, 100 mmol) in THF (100 mL) was added a 2 M solution of LDA (55.0 mL, 110 mmol) in THF over a 15 min period while maintaining the temperature below −40° C. After the addition, the temperature was maintained at −40° C. After 20 min at −40° C., the reaction mixture was cooled to −78° C. and $ZnCl_2$ (15.2 g, 111 mmol) was added in several portions. The mixture was warmed to −40° C. After 20 min, acetaldehyde (7.00 mL, 125 mmol) was added and the reaction was allowed to warm to −20° C. After 30 min, the reaction was quenched with saturated aqueous $NH_4Cl$ (200 mL), diluted with brine (200 mL) and extracted with ethyl acetate (EtOAc) (3×100 mL). The combined organic layers were washed with saturated aqueous $NH_4Cl$ (75 mL), 1 N aqueous HCl (3×75 mL), brine (75 mL), saturated aqueous $NaHCO_3$ (2×75 mL), brine (2×75 mL), dried ($MgSO_4$), filtered and concentrated. The crude residue was diluted with hexanes (100 mL), chilled (0° C.) and the white solid was collected by filtration washing with hexanes to afford 10 (10.95 g, 64%) as a 85:15 mixture of diastereomers that were used without further purification. Major diastereomer 10: $^{13}C$ NMR (75 MHz, $CDCl_3$) δ 221.13 (s), 71.59 (d), 52.10 (s), 41.40 (d), 37.09 (t), 36.49 (t), 21.11 (t), 15.86 (q), 15.81 (q), 14.67 (q); minor diastereomer b 216.81 (s), 69.95 (d), 53.28 (s), 41.31 (d), 37.53 (t), 35.81 (t), 20.53 (t), 17.39 (q), 16.05 (q), 15.19 (q).

(2S*,6R*)-2,6-Dimethyl-2-ethenylcyclohexanone (11): A mixture of 10 (2.50 g, 14.7 mmol) and Martin's sulfurane (10.0 g, 14.9 mmol) in toluene (30 mL) was warmed at reflux. After 3 h, TLC ($Et_2O$:hexanes, 5:95) indicated starting material was consumed and GC-EIMS indicated a mixture of diastereomeric ketone 11 and 15 (79:21). The reaction was cooled to room temperature, diluted with hexanes (100 mL) and passed through a pad of silica gel eluting first with hexanes and then 5% $Et_2O$ in hexanes. The material from the pad was purified on silica gel using $Et_2O$-hexanes (1:99, the 2:98, then 3:97) to afford 11 (1.1 g, 51%) as a volatile liquid. Data for 11IR (neat) 2968, 2929, 2856, 1707, 1450 $cm^{-1}$; $^1H$ NMR (300 MHz, $CDCl_3$) δ 5.96 (dd, J=17.6, 10.7 Hz, 1H), 5.13 (d, J=10.7 Hz, 1H), 4.95 (d, J=17.6 Hz, 1H), 2.79-2.61 (m, 1H), 2.10-1.96 (m, 2H), 1.95-1.77 (m, 1H), 1.72-1.48 (m, 2H), 1.43-1.22 (m, 1H), 1.12 (s, 3H), 0.99 (d, J=6.5 Hz, 3H); $^{13}C$ NMR (75 MHz, $CDCl_3$) δ 214.21 (q), 142.79 (d), 115.14 (t), 52.28 (s), 41.99 (d), 40.81 (t), 36.91 (t), 24.42 (q), 21.92 (t), 14.82 (q); GC-EIMS m/z: (% rel. abundance) 152 (52), 109 (38), 94 (85), 68 (100). Purification of the second eluting diastereomer 15 was complicated by the presence of co-eluting 1,1,1,3,3,3-hexafluoro-2-phenyl-2-propanol, a by-product of the dehydrating agent.

tert-Butyl 1-((1R*,2S*,6R*)-1-hydroxy-2,6-dimethyl-2-ethenylcyclohexyl) acetate (12A) and tert-butyl 1-((1S*,2S*,6R*)-1-hydroxy-2,6-dimethyl-2-ethenylcyclohexyl) acetate (12B): To a chilled (−50° C.) solution of I-butyl acetate (1.86 g, 16.0 mmol) in THF (16 mL) was added a 1 M solution of LiHMDS (15.0 mL, 15.0 mmol) in THF over a 10 min period while maintaining the temperature below −40° C. After 20 min, the mixture was cooled to −70° C. and 11 (1.52 g, 10.0 mmol) in THF (5 mL) was added dropwise over 5 minutes. After 2 h, the reaction was quenched with saturated aqueous $NH_4Cl$ (100 mL) and extracted with MTBE (3×75 mL). The combined organic layers were washed with saturated aqueous $NH_4Cl$ (2×30 mL), 1 N aqueous HCl (2×30 mL), brine (30 mL), saturated aqueous $NaHCO_3$ (2×30 mL), brine (30 mL), dried ($MgSO_4$), filtered and concentrated to afford a 82:12 mixture of 12A and 12B by $^1H$ NMR. The crude material was purified on silica gel eluting with a gradient of 0-4% EtOAc in hexanes to afford first 12A (1.88 g, 70%) as a clear oil: IR (neat) 3447 (broad), 2929, 1700, 1147 $cm^{-1}$; $^1H$ NMR (300 MHz, $CDCl_3$) δ 6.19 (ddd, J=17.3, 11.2, 1.1 Hz, 1H), 5.14-5.00 (m, 2H), 2.44 (dd, J=16.2, 1.1 Hz, 1H), 2.17 (dd, J=16.1, 1.1 Hz, 1H), 1.92-1.75 (m, 1H), 1.75-1.54 (m, 1H), 1.45 (s, 6H), 1.61-1.37 (m, 4H), 1.33 (s, 1H), 1.30-1.18 (m, 1H), 1.06 (d, J=1.1 Hz, 3H), 0.86 (dd, J=6.4, 1.1 Hz, 3H); $^{13}C$ NMR (75 MHz, $CDCl_3$) δ 174.83 (s), 142.64 (d), 113.90 (t), 81.62 (s), 75.19 (s), 45.60 (s), 38.15 (t), 38.09 (d), 35.17 (t), 30.49 (t), 28.01 (q), 21.67 (q), 21.47 (t), 16.67 (q); GC-EIMS m/z (% rel. abundance) 212 (9), 194 (31), 96 (100); and second 12B (450 mg, 17%) as a clear oil that solidified upon standing: IR (neat) 3451 (broad), 2978, 2936, 1702, 1152 cm$^{-1}$; $^{1}$H NMR (300 MHz, CDCl$_3$) δ 6.40 (dd, J=17.9, 11.2 Hz, 1H), 5.10 (dd, J=11.2, 1.6 Hz, 1H), 5.03 (dd, J=17.8, 1.5 Hz, 1H), 2.50 (d, J=16.1 Hz, 1H), 2.42 (d, J=16.1 Hz, 1H), 1.99-1.81 (m, 1H), 1.81-1.71 (m, 1H), 1.70-1.51 (m, 2H), 1.46 (s, 9H), 1.44-1.34 (m, 2H), 1.20-1.03 (m, 1H), 1.00 (s, 3H), 0.92 (d, J=6.8 Hz, 3H); $^{13}$C NMR (75 MHz, CDCl$_3$) δ 174.70 (s), 143.69 (d), 112.68 (t), 81.79 (s), 76.77 (s), 46.05 (s), 38.83 (d), 34.44 (t), 33.32 (t), 31.25 (t), 28.02 (q), 24.65 (q), 20.79 (t), 16.25 (q); GC-EIMS m/z (% rel. abundance) 212 (9), 194 (31), 96 (100).

tert-Butyl 1-((1R*,2S*,6R*)-1-acetoxy-2,6-dimethyl-2-ethenylcyclohexyl) acetate (13): To a solution of 12A (1.72 g, 6.41 mmol) in acetonitrile (CH$_3$CN) (12 mL) was added isopropenyl acetate (12.0 mL, 109 mmol), cyclohexanone oxime (72 mg, 0.64 mmol) and then p-TsOH.H$_2$O (57 mg, 0.30 mmol). The reaction was warmed at 50° C. After 18 h, the reaction was diluted with saturated aqueous NH$_4$Cl (50 mL) and extracted with hexanes (3×30 mL). The combined organic layers were washed with saturated aqueous NH$_4$Cl (2×15 mL), brine (15 mL), saturated aqueous NaHCO$_3$ (2×15 mL), brine (2×15 mL), dried (MgSO$_4$), filtered and concentrated. The crude material was purified on silica gel eluting with a 0-2% gradient of EtOAc in hexanes to afford 13 (1.55 g, 78%) as a clear oil: IR (neat) 2976, 2933, 1734, 1151 cm$^{-1}$; $^{1}$H NMR (300 MHz, CDCl$_3$) δ 6.20 (dd, J=17.5, 11.0 Hz, 1H), 5.50-4.81 (m, 2H), 3.17 (s, 2H), 2.44 (q, J=6.9 Hz, 1H), 2.08 (s, 3H), 1.77 (ddd, J=12.8, 11.1, 4.3 Hz, 1H), 1.57-1.43 (m, 3H), 1.39 (s, 9H), 1.12 (s, 3H), 1.03 (d, J=6.8 Hz, 3H); $^{13}$C NMR (75 MHz, CDCl$_3$) δ 170.61 (s), 169.86 (s), 142.30 (d), 114.17 (t), 88.51 (s), 79.97 (s), 46.01 (s), 37.26 (t), 36.25 (d), 35.75 (t), 30.16 (t), 28.02 (q), 22.98 (q), 22.53 (q), 20.40 (t), 17.95 (q); GC-EIMS m/z (% rel. abundance) 254 (3), 236 (7), 194 (62), 138 (59), 57 (100).

(±)-Epianastrephin (1): To a chilled (0° C.) solution of 13 (1.01 g, 3.26 mmol) in CH$_3$CN (24 mL) was added a solution of BF$_3$.Et$_2$O (≥46.5% BF$_3$ basis, 400 μL, 3.26 mmol) in CH$_3$CN (5 mL). The reaction was monitored by TLC (EtOAc:hexanes, 5:95). After 3 h, the reaction was diluted with saturated aqueous NaHCO$_3$ (20 mL) and extracted with hexanes (3×50 mL). The combined organic layers were washed with saturated aqueous NaHCO$_3$ (3×25 mL), brine (3×25 mL), dried (MgSO$_4$), filtered and concentrated to afford 575 mg of crude material. The crude material was adsorbed onto silica gel and purified on silica gel eluting with a 0-6% gradient of EtOAc in hexanes to afford 316 mg (50%) of 1 as an oil: mp (white crystals from hexanes): 31-32° C.; IR (neat) 2942, 2871, 1780, 1016 cm$^{-1}$; $^{1}$H NMR (300 MHz, CDCl$_3$) δ 5.68 (dd, J=17.6, 10.6 Hz, 1H), 5.00 (d, J=1.5 Hz, 1H), 4.95 (dd, J=4.7, 0.8 Hz, 1H), 2.38 (dd, J=16.4, 14.8 Hz, 1H), 2.24 (dd, J=16.4, 6.4 Hz, 1H), 2.10 (dd, J=14.8, 6.4 Hz, 1H), 2.01 (dd, J=7.9, 3.0 Hz, 1H), 1.84 (ddd, J=8.2, 6.2, 3.9 Hz, 1H), 1.73-1.59 (m, 2H), 1.59-1.43 (m, 2H), 1.38 (s, 3H), 1.06 (s, 3H); $^{13}$C NMR (75 MHz, CDCl$_3$) δ 176.12 (s), 147.76 (d), 111.59 (t), 86.03 (s), 53.43 (d), 38.46 (s), 37.90 (t), 37.02 (t), 29.46 (t), 20.90 (q), 20.43 (t), 16.37 (q); GC-EIMS m/z (% rel. abundance) 194 (2), 179 (25), 135 (26), 108 (59), 81 (100). ($^{1}$H and $^{13}$C spectral data for compound 1 was identical to literature data, see: Baker, J. D., and Heath, R. R., J. Chem. Ecol., 19: 1511 (1993)).

The synthesis of the diastereomer of (±)-epianastrephin (1) described in Example 1, (±)-apianastrephin (2), is carried out as exemplified below.

Example 2

Synthesis of (±)-anastrephin (2)

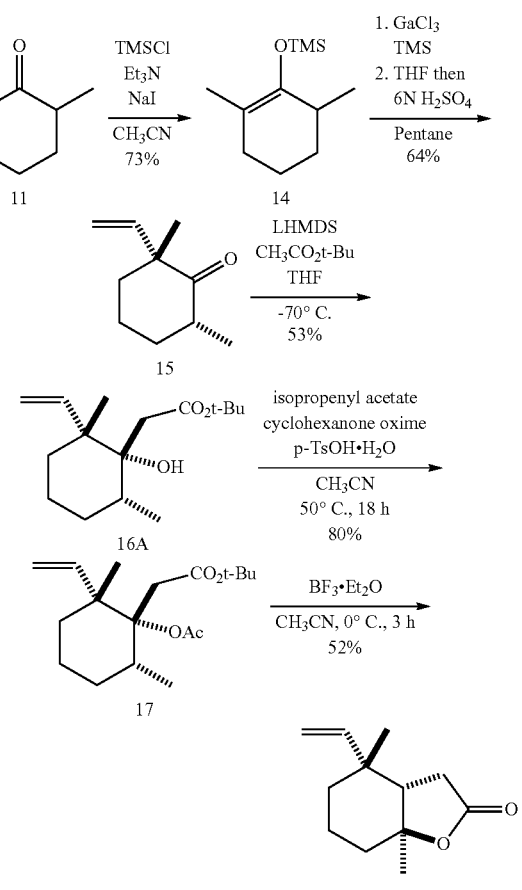

Trimethyl-(2,6-dimethylcyclohex-1-enyloxy)silane (14): To a solution of 11 (12.6 g, 100 mmol) in CH$_3$CN (125 mL) was added TMSCl (15.9 mL, 125 mmol), Et$_3$N (17.4 mL, 125 mmol) and then NaI (18.75 g, 125.1 mmol) in several portions. After 18 h, the reaction was diluted with ice cold saturated aqueous NH$_4$Cl (250 mL) and extracted with pentane (3×100 mL). The combined pentane layers were washed with saturated aqueous NH$_4$Cl (3×100 mL), brine (3×100 mL), dried (MgSO$_4$), filtered and reduced in volume (20 mL). The crude mixture was then passed through a pad of silica gel eluting with 0-2% ether-pentane to afford 14 (14.6 g, 73%) as a clear oil: $^{13}$C NMR (75 MHz, CDCl$_3$) δ 147.16, 112.15, 34.22, 32.41, 30.93, 22.51, 20.63, 19.07, 16.95, 14.20, 0.73; GC-EIMS m/z (% rel. abundance) 198 (64), 183 (96), 72 (100).

(2R*,6R*)-2,6-Dimethyl-2-ethenylcyclohexanone (15): To a chilled (ice water bath) solution of 14 (9.36 g, 47.3 mmol) in pentane was added TMSA (8.10 g 82.5 mmol) followed by a solution of GaCl$_3$ (25.0 g, 142 mmol) in pentane (142 mL) over 15 minutes. After another 30 min, the mixture was diluted with THF (250 mL). After another 30 min, a 6 N aqueous solution of H$_2$SO$_4$ (75 mL) was added dropwise. After 30 min, the solution was diluted with brine (400 mL) and filtered through Celite® washing with pentane. The filtrate was extracted with pentane (3×250 mL).

The combined organic layers were washed with brine (3×150 mL), saturated aqueous NaHCO$_3$ (2×150 mL), water (3×100 mL), brine (3×100 mL), dried (MgSO$_4$), filtered and concentrated. The residue was passed through a pad of silica gel (350 mL funnel) eluting with ether-hexanes (0-4%) to afford partially purified material (5.74 g, 80%) as a 8:1:1 mixture of 15:11:9, respectively, by $^1$H NMR. Data for 15: IR (neat) 2967, 2931, 2869, 1702, 1451 cm$^{-1}$; $^1$H NMR (300 MHz, CDCl$_3$) δ 6.19 (dd, J=17.7, 11.0 Hz, 1H), 5.09 (dd, J=11.0, 1.1 Hz, 1H), 5.00 (dd, J=17.7, 1.1 Hz, 1H), 2.69 (hept, J=6.5 Hz, 1H), 2.12-2.00 (m, 1H), 1.97-1.83 (m, 1H), 1.82-1.76 (m, 2H), 1.75-1.69 (m, 1H), 1.39 (td, J=12.6, 3.8 Hz, 1H), 1.30 (s, 3H), 1.01 (d, J=6.5 Hz, 3H); 13C NMR (75 MHz, CDCl$_3$) δ 215.46 (s), 143.32 (d), 112.10 (t), 50.83 (s), 41.14 (d), 38.73 (t), 36.02 (t), 22.71 (q), 21.07 (t), 15.26 (q); GC-EIMS m/z (% rel. abundance) 152 (51), 109 (38), 94 (77), 68 (100).

tert-Butyl 1-((1R*,2R*,6R*)-1-hydroxy-2,6-dimethyl-2-ethenylcyclohexyl) acetate (16A) and tert-butyl 1-((1S*,2R*,6R*)-1-hydroxy-2,6-dimethyl-2-ethenylcyclohexyl) acetate (16B): To a chilled (−50° C.) solution of t-butyl acetate (1.45 g, 12.5 mmol) in THF (20 mL) was added a 1 M solution of LiHMDS (12.0 mL, 12.0 mmol) in THF over a 10 min period while maintaining the temperature below −40° C. After 20 min at −50° C., the mixture was cooled to −75° C. and 15 (1.52 g, 10.0 mmol) in THF (5 mL) was added dropwise over 5 min while maintaining the temperature below −70° C. After 1.75 h, the mixture was quenched with saturated aqueous NH$_4$Cl (150 mL) and extracted with hexanes (3×60 mL). The combined organic layers were washed with brine (2×30 mL), 1 N aqueous HCl (2×30 mL), brine (30 mL), saturated aqueous NaHCO$_3$ (2×30 mL), brine (30 mL), dried (MgSO$_4$), filtered and concentrated to afford a 58:42 mixture of 16A and 16B by $^1$H NMR. The crude material was adsorbed onto silica gel and purified on silica gel eluting with a gradient of 0-4% EtOAc in hexanes to afford first 16A (1.37 g, 53%) as a clear oil: IR (neat) 3443 (broad), 2977, 2933, 1699, 1149 cm$^{-1}$; $^1$H NMR (300 MHz, CDCl$_3$) δ 6.28 (dd, J=17.7, 11.0 Hz, 1H), 5.10-4.94 (m, 2H), 2.46 (d, J=15.9 Hz, 1H), 2.17 (d, J=15.9, 1.0 Hz, 1H), 2.08-1.87 (m, 1H), 1.81-1.68 (m, 1H), 1.43 (s, 9H), 1.31 (s, 1H), 1.03 (s, 3H), 0.84 (d, J=6.6, 3H); $^{13}$C NMR (75 MHz, CDCl$_3$) δ 174.64 (s), 146.49 (d), 112.75 (t), 81.65 (s), 75.33 (s), 45.28 (s), 38.78 (t), 37.22 (d), 34.43 (t), 30.53 (t), 28.05 (q), 21.50 (t), 17.91 (q), 16.74 (q); GC-EIMS m/z (% rel. abundance) 212 (14), 194 (42), 96 (100); and second 827 mg (31%) of 16B as an oil: IR (neat) 3446, 2978, 2931, 1701, 1152 cm$^{-1}$; $^1$H NMR (300 MHz, CDCl$_3$) δ 6.16 (dd, J=17.7, 11.0 Hz, 1H), 5.41 (s, 1H), 5.03-4.87 (m, 2H), 2.50-2.28 (m, 2H), 2.00 (ddd, J=13.5, 6.7, 3.6 Hz, 1H), 1.64-1.34 (m, 5H), 1.44 (s, 9H), 1.11 (s, 4H), 0.89 (d, J=6.7 Hz, 3H); $^{13}$C NMR (75 MHz, CDCl$_3$) δ 174.90 (s), 146.17 (d), 111.93 (t), 81.62 (s), 76.21 (s), 45.44 (s), 37.35 (d), 33.47 (t), 32.06 (t), 31.40 (t), 28.05 (q), 20.80 (t), 20.03 (q), 16.32 (q); GC-EIMS m/z (% rel. abundance) 269 (0.6), 212 (9), 194 (30), 96 (100).

tert-Butyl 1-((1R*,2R*,6R*)-1-acetoxy-2,6-dimethyl-2-ethenylcyclohexyl) acetate (17): To a solution of 16A (850 mg, 3.17 mmol) in CH$_3$CN (6.5 mL) and isopropenyl acetate (6.5 mL, 59 mmol) was added cyclohexanone oxime (39 mg, 0.34 mmol) followed by p-TsOH.H$_2$O (33 mg, 0.17 mmol). The reaction was warmed at 50° C. After 45 h, the mixture was diluted with saturated aqueous NH$_4$Cl (100 mL) and extracted with hexanes (3×50 mL). The combined organic layers were washed with brine (3×30 mL), saturated aqueous NaHCO$_3$ (3×30 mL), brine (3×30 mL), dried (MgSO$_4$), filtered and concentrated. The crude material was purified on silica gel eluting with a 0-4% gradient of EtOAc in hexanes to afford 17 (793 mg, 80%) as a clear oil: IR (neat) 2976, 2935, 1730, 1149 cm$^{-1}$; $^1$H NMR (300 MHz, CDCl$_3$) δ 6.12 (dd, J=17.6, 11.0 Hz, 1H), 5.02 (ddd, J=17.8, 11.2, 1.6 Hz, 2H), 3.32 (d, J=15.9 Hz, 1H), 3.17 (d, J=15.9 Hz, 1H), 2.46-2.31 (m, 1H), 2.06 (s, 3H), 1.90 (m, 1H), 1.57-1.45 (m, 1H), 1.41 (s, 9H), 1.21-1.12 (m, 1H), 1.11 (s, 3H), 1.01 (d, J=6.8 Hz, 3H); $^{13}$C NMR (75 MHz, CDCl$_3$) δ 170.55 (s), 169.94 (s), 145.02 (d), 112.40 (t), 89.06 (s), 80.17 (s), 45.68 (s), 37.51 (t), 35.88 (d), 35.00 (t), 30.31 (t), 28.04 (q), 22.62 (q), 20.97 (q), 20.45 (t), 17.94 (q).

(±)-Anastrephin (2): To a chilled (0° C.) solution of 17 (1.01 g, 3.26 mmol) in CH$_3$CN (24 mL) was added a solution of BF$_3$.Et$_2$O (≥46.5% BF$_3$ basis, 425 μL, 3.44 mmol) in CH$_3$CN (5 mL). After 3 h, the reaction was diluted with saturated aqueous NaHCO$_3$ (20 mL) and extracted with hexanes (3×50 mL). The combined organic layers were washed with saturated aqueous NaHCO$_3$ (3×25 mL), brine (3×25 mL), dried (MgSO$_4$), filtered and concentrated to afford 524 mg of crude material. The crude material was adsorbed onto silica gel and purified on silica gel eluting with a 0-6% gradient of EtOAc in hexanes to afford 330 mg (52%) of 2 as a white solid: mp (from hexanes) 83-84° C.; IR (neat) 2942, 2868, 1770, 1029 cm$^{-1}$; $^1$H NMR (300 MHz, CDCl$_3$) δ 5.89 (ddd, J=17.4, 11.2, 0.9 Hz, 1H), 5.19-5.03 (m, 2H), 2.65-2.30 (m, 3H), 2.16-1.94 (m, 3H), 1.31 (dd, J=13.1, 5.3, 1H), 1.26 (s, 3H), 1.04 (s, 3H); $^{13}$C NMR (75 MHz, CDCl$_3$) δ 176.14 (s), 139.98 (d), 112.94 (t), 86.34 (s), 55.51 (d), 38.62 (s), 37.19 (t), 36.07 (t), 30.35 (q), 29.01 (t), 20.38 (t), 20.21 (q); GC-EIMS m/z (% rel. abundance) 194 (4), 179 (37), 136 (37), 108 (63), 81 (100). ($^1$H and $^{13}$C spectral data for compound 2 was identical to literature data, see: Baker, J. D., and Heath, R. R., J. Chem. Ecol., 19: 1511 (1993)).

Example 3

Synthesis of (3aS*,4S*,7aS*)-4,7a-Dimethyl-4-ethylhexahydrobenzofuran-2(3H)-one (18)

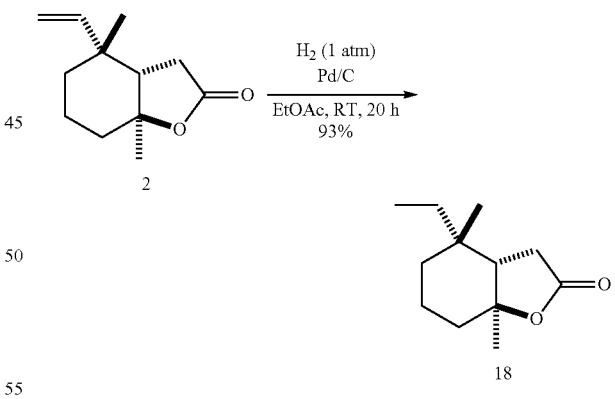

To a solution of 2 (107 mg, 0.551 mmol) in EtOAc (8 mL) was added 10% palladium on carbon (14 mg). The flask was evacuated under vacuum and refilled with hydrogen gas three times. The reaction stirred under 1 atmosphere of hydrogen for 20 hours. The reaction mixture was then filtered through Celite® and concentrated to afford 101 mg (93%) of 21 as an oil that solidified under house vacuum. Recrystallization (hexanes) gave 47 mg of 21 as white needles from two crops: IR (neat) 2939, 2871, 1770, 1028, 954, 928 cm$^{-1}$, $^1$H NMR (300 MHz, CDCl$_3$) δ 2.49 (dd, J=16.3, 14.9 Hz, 1H), 2.31 (dd, J=16.3, 6.5 Hz, 1H), 2.15-1.90 (m, 2H), 1.85-1.69 (m, 2H), 1.68-1.40 (m, 3H), 1.36 (s, 3H), 1.33-1.24 (m, 1H), 1.19-0.97 (m, 1H), 0.91 (s, 3H), 0.85 (t, J=7.5 Hz, 3H), $^{13}$C NMR (75 MHz, CDCl$_3$) δ 176.62 (s), 86.57 (s), 56.81 (d), 37.68 (t), 36.36 (t), 35.68 (s), 29.40 (t), 27.64 (q), 24.44 (t), 21.08 (q), 20.53 (t), 9.05 (q); GC-EIMS m/z (% rel. abundance) 181 (70), 167 (37), 153 (73), 139 (25), 81 (93), 55 (100).

Example 4

Synthesis of (3aS*,4R*,7aS*)-4,7a-Dimethyl-4-ethyl hexahydrobenzofuran-2(3H)-one (20)

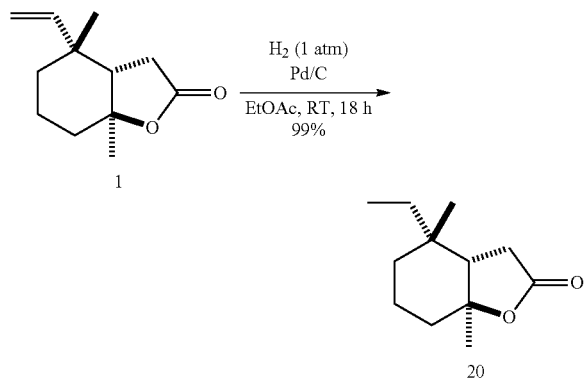

To a solution of 1 (260 mg, 1.34 mmol) in EtOAc (10 mL) was added 10% palladium on carbon (29 mg). The flask was evacuated under vacuum and refilled with hydrogen gas three times. The reaction stirred under 1 atmosphere of hydrogen for 18 hours. To the reaction mixture was added Celite® and the reaction was filtered through Celite® and concentrated to afford 262 mg (99%) of 22 as an oil that partially solidified under house vacuum: IR (neat) 2940, 1767, 1020, 955, 920 cm$^{-1}$; $^{1}$H NMR (300 MHz, CDCl$_3$) δ 2.40 (t, J=16.4, 14.5 Hz, 1H), 2.29 (dd, J=16.3, 6.8 Hz, 1H), 1.98 (dd, J=14.8, 7.0 Hz, 2H), 1.86-1.74 (m, 1H), 1.65-1.57 (m, 2H), 1.53-1.43 (m, 1H), 1.36 (s, 3H), 1.34-1.11 (m, 3H), 0.88 (s, 3H), 0.83 (t, J=7.5 Hz, 3H), $^{13}$C NMR (75 MHz, CDCl$_3$) δ 176.40 (s), 86.54 (s), 54.51 (d), 37.14 (t), 36.65 (t), 36.12 (t), 35.11 (s), 29.19 (t), 20.76 (q), 20.35 (t), 16.95 (q), 7.53 (q); GC-EIMS m/z (% rel. abundance) 181 (78), 167 (41), 153 (64), 139 (31), 81 (100).

Example 5

Synthesis of (3aS*,7aS*)-2-Oxo-4,4,7a-trimethyloctahydrobenzofuran (24)

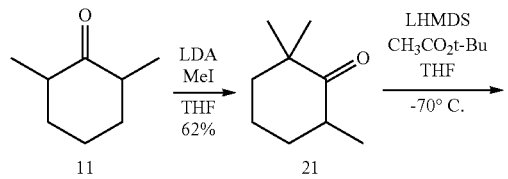

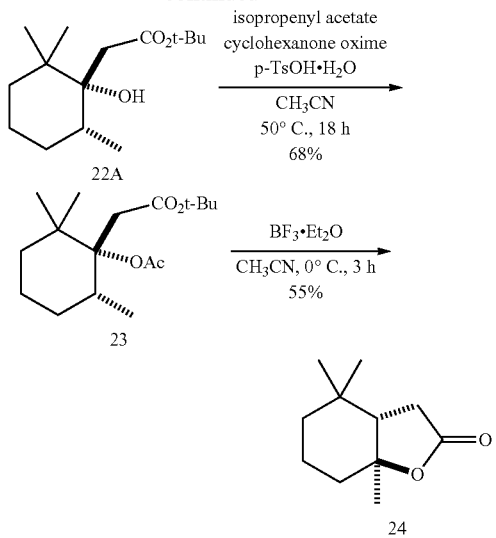

2,2,6-Dimethylcyclohexanone (21) (prepared according to Jung, M. E., Murakami, M., Org. Lett., 8: 5857 (2006)): To a chilled (−40° C.) solution of 11 (6.18 g, 49.0 mmol) in THF (50 mL) was added a 2 M solution of LDA (24.5 mL, 49.0 mmol) in THF. After 40 minutes, iodomethane (4.57 mL, 73.4 mmol) was added in several portions. The mixture stirred at −40° C. for 4 hours and was then allowed to warm to room temperature. After 6 hours, the reaction was quenched with saturated aqueous NH$_4$Cl (250 mL) and extracted with hexanes (3×100 mL). The combined organic layers were washed with saturated aqueous NH$_4$Cl (2×50 mL), brine (3×50 mL), dried (MgSO$_4$), filtered and concentrated. The crude material was diluted with hexanes and passed through a pad of silica gel (600 mL funnel) eluting with 0-2% Et$_2$O-hexanes to afford 21 (4.25 g, 62%) as a clear oil: $^{1}$H NMR (300 MHz, CDCl$_3$) δ 2.74-2.57 (m, 1H), 2.12-1.98 (m, 1H), 1.97-1.70 (m, 2H), 1.70-1.48 (m, 2H), 1.40-1.23 (m, 1H), 1.17 (s, 3H), 1.04 (s, 3H), 0.98 (d, J=6.5 Hz, 3H); GC-EIMS m/z (% rel. abundance) 140 (84), 82 (100).

tert-Butyl 1-((1R*,6R*)-1-hydroxy-2,2,6-trimethylcyclohexyl) acetate (22A) and tert-butyl 1-((1S*,6R*)-1-hydroxy-2,2,6-trimethylcyclohexyl) acetate (22B): To a chilled (−50° C.) solution of t-butyl acetate (4.98 g, 42.9 mmol) in THF (50 mL) was added a 2 M solution of LDA (21.5 mL, 43.0 mmol) in THF over a 20 min period while maintaining the temperature below −40° C. After 30 min, the mixture was cooled to −70° C. and 21 (4.25 g, 30.3 mmol) in THF (20 mL) was added dropwise over 15 minutes. After 3 h, the reaction was quenched with saturated aqueous NH$_4$Cl (250 mL) and extracted with hexanes (3×150 mL). The combined organic layers were washed with saturated aqueous NH$_4$Cl (2×50 mL), brine (2×50 mL), 1 N aqueous HCl (2×50 mL), brine (2×50 mL), saturated aqueous NaHCO$_3$ (2×50 mL), brine (2×50 mL), dried (MgSO$_4$), filtered and concentrated to afford an ~3:1 mixture of 22A and 22B by $^{1}$H NMR. The crude material was partially purified on a pad of silica gel (600 mL funnel) eluting with a gradient of 0-2° % Et$_2$O in hexanes to afford first 22A (2.48 g, 32%) as a clear oil: IR (neat) 3459 (broad), 2931, 1701, 1147 cm$^{-1}$; $^{1}$H NMR (300 MHz, CDCl$_3$) δ 4.69 (broad, 1H), 2.48 (d, J=15.8 Hz, 1H), 2.23 (d, J=15.8 Hz, 1H), 1.85-1.65 (m, 2H), 1.63-1.53 (m, 1H), 1.46 (s, 9H), 1.42-1.48 (m, partially obscured by singlet at 1.46 ppm, 2H), 1.36-1.21 (m, 1H), 1.09-0.99 (m, 1H), 0.95 (s, 3H), 0.91 (s, 3H), 0.85 (d, J=6.6 Hz, 3H); $^{13}$C NMR (75 MHz, CDCl$_3$) δ 174.72 (s), 81.57 (s), 75.86 (s), 39.07 (s), 37.97 (t), 37.19 (d), 36.45 (t), 30.77 (t), 27.99 (q), 25.94 (q), 22.77 (q), 21.80 (t), 16.78 (q); GC-EIMS m/z (% rel. abundance) 200 (93), 183 (10), 140 (55), 82 (100); then a 7.2:1 mixture of 22A:22B (3.13 g, 40%); and second 22B (1.28 g, 16%): IR (neat) 3459 (broad), 2928, 1701, 1147 cm$^{-1}$; $^1$H NMR (300 MHz, CDCl$_3$) δ 5.19 (broad, 1H), 2.47 (d, J=16.1 Hz, 1H), 2.38 (d, J=16.1 Hz, 1H), 2.05-1.87 (m, 1H), 1.63-1.48 (m, 3H), 1.46 (s, 9H), 1.38-1.29 (m, 2H), 1.12-1.05 (m, 1H), 1.03 (s, 3H), 0.91 (d, partially obscured by singlet at 0.91 ppm, J=6.8 Hz, 3H), 0.91 (s, 3H); $^{13}$C NMR (75 MHz, CDCl$_3$) δ 175.07 (s), 81.62 (s), 76.85 (s), 39.90 (s), 37.83 (t), 37.43 (d), 32.84 (t), 31.57 (t), 27.98 (q), 26.36 (q), 22.15 (q), 21.31 (t), 16.40 (q); GC-EIMS m/z (% rel. abundance) 200 (93), 183 (12), 140 (54), 82 (100).

tert-Butyl 1-((1R*,6R*)-1-acetoxy-2,2,6-trimethylcyclohexyl) acetate (23): To a solution of 22A (2.36 g, 9.20 mmol) in CH$_3$CN (9 mL) was added isopropenyl acetate (9.0 mL, 81 mmol), cyclohexanone oxime (42 mg, 0.37 mmol) and then p-TsOH.H$_2$O (32 mg, 0.17 mmol). The reaction was warmed at 50° C. After 18 h, the reaction cooled to room temperature, diluted with saturated aqueous NaHCO$_3$ (200 mL) and extracted with hexanes (3×75 mL). The combined organic layers were washed with saturated aqueous NaHCO$_3$ (2×50 mL), brine (2×50 mL), saturated aqueous NH$_4$Cl (2×50 mL), brine (2×50 mL), dried (MgSO$_4$), filtered and concentrated. The crude material was purified on silica gel eluting with a 0-5% gradient of EtOAc in hexanes to afford 23 (1.86 g, 68%) as a clear oil: IR (neat) 2976, 2932, 1729, 1148 cm$^{-1}$; $^1$H NMR (300 MHz, CDCl$_3$) δ 3.34 (d, J=15.8 Hz, 1H), 3.21 (d, J=15.8 Hz, 1H), 2.42-2.24 (m, 1H), 2.05 (s, 3H), 1.78-1.63 (m, 1H), 1.55-1.39 (m, partially obscured by singlet at 1.42 ppm, 4H), 1.42 (s, 9H), 1.18-1.05 (m, 1H), 1.03 (d, partially obscured by singlets at 1.00 ppm, J=6.6 Hz, 3H), 1.00 (s, 6H); $^{13}$C NMR (75 MHz, CDCl$_3$) δ 170.78 (s), 170.28 (s), 90.32 (s), 80.18 (s), 40.52 (s), 37.81 (t), 37.03 (t), 35.75 (d), 30.63 (t), 28.01 (q), 27.08 (q), 24.26 (q), 22.64 (q), 21.15 (t), 18.15 (q).

(3aS*,7aS*)-2-Oxo-4,4,7a-trimethyloctahydrobenzofuran (24): To a chilled (0° C.) solution of 23 (1.73 g, 3.26 mmol) in CH$_3$CN (30 mL) was added a solution of BF$_3$.Et$_2$O (≥46.5% BF; basis, 250 μL, 2.02 mmol) in CH$_3$CN (2.5 mL). The reaction was monitored by TLC (EtOAc:hexanes, 5:95). After 3.5 h, the reaction was diluted with saturated aqueous NaHCO$_3$ (40 mL), concentrated to remove excess CH$_3$CN and extracted with hexanes (3×75 mL). The combined organic layers were washed with saturated aqueous NaHCO$_3$ (2×40 mL), brine (2×40 mL), saturated aqueous NH$_4$Cl (2×40 mL), brine (2×40 mL), dried (MgSO$_4$), filtered and concentrated to afford 930 mg of crude material. The crude material was adsorbed onto silica gel and purified on silica gel eluting with a 0-10% gradient of EtOAc in hexanes to afford 24 (581 mg, 55%) as an oil: mp (from hexanes) 78-79° C.; IR (neat) 2944, 2869, 1769, 1030, 1008 cm$^{-1}$; $^1$H NMR (300 MHz, CDCl$_3$) δ 2.42 (dd, J=16.2, 14.7 Hz, 1H), 2.29 (dd, J=16.3, 6.7 Hz, 1H), 2.06-1.88 (m, 2H), 1.85-1.71 (m, 1H), 1.70-1.49 (m, 3H), 1.34 (s, 3H), 1.32-1.20 (m, 1H), 0.95 (s, 3H), 0.92 (s, 3H); $^{13}$C NMR (75 MHz, CDCl$_3$) δ 176.41 (s), 86.47 (s), 55.55 (d), 40.05 (t), 37.17 (t), 32.70 (s), 32.24 (q), 29.19 (t), 20.70 (t), 20.45 (q), 19.79 (q); GC-EIMS m/z (% rel. abundance) 182 (1), 167 (87), 139 (96), 109 (25), 69 (100). ($^1$H and $^{13}$C spectral data for compound 24 was identical to literature data, see: Imamura, P. M., and Santiago, G. M. P., Synthetic Communications, 27: 2479 (1997)).

Example 6

Isomerization of (2R*,6R*)-2,6-dimethyl-2-ethenyl-cyclohexanone (15) to (2S*,6R*)-2,6-Dimethyl-2-ethenylcyclohexanone (11)

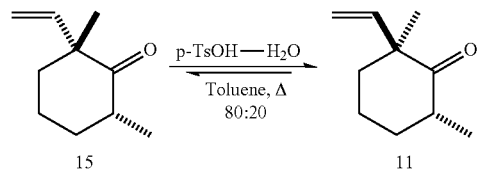

A mixture of 15 (1.01 g, 6.64 mmol) and p-TsOH.H$_2$O (55 mg, 0.29 mmol) in toluene (2 mL) was warmed at reflux. After 45 min, the reaction was cooled to room temperature, diluted with hexanes (10 mL), treated with decolorizing carbon, filtered through Celite® washing first with hexanes and then Et$_2$O. The mixture was reduced in volume (~15 mL) in vacuo (caution the cyclohexanones are volatile liquids). A crude $^1$H NMR indicated an equilibrium mixture of 11 and 15 (80:20). The mixture was adsorbed onto silica gel and purified on silica gel eluting with 2% Et$_2$O in hexanes to afford first 630 mg (63%) of 11 and second 128 mg (13%) of recovered 15 as volatile oils. $^1$H NMR spectral data for compounds 11 and 15 were identical to that reported for compounds 11 and 15 in Examples 1 and 2 above.

Example 7

Synthesis of the aglycon 7 of suspensosides A and B (8)

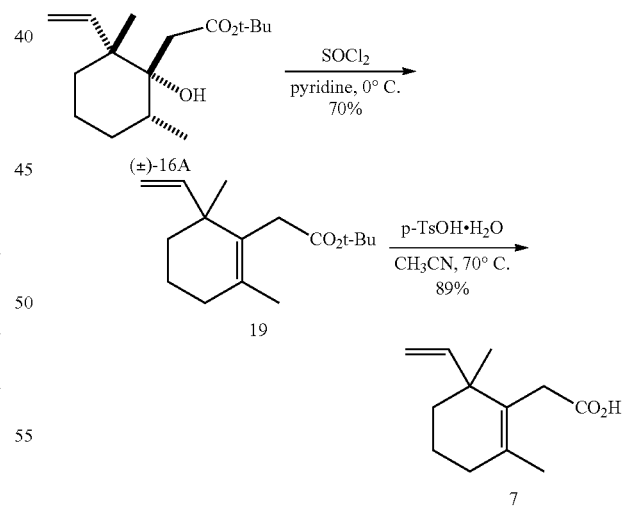

tert-Butyl 2-(2,6-dimethyl-2-ethenylcyclohex-1-enyl) acetate (19): To a chilled (0° C.) solution of 16A (600 mg, 2.29 mmol) in pyridine (6 mL) was added SOCl$_2$ (240 μL, 3.32 mmol) in several portions while maintaining the temperature below 0° C. After 1.5 h, the mixture was diluted with 1 N aqueous HCl (150 mL) and extracted with hexanes (3×35 mL). The combined organic layers were washed with 1 N aqueous HCl (3×30 mL), brine (30 mL), saturated aqueous NaHCO$_3$ (2×30 mL), brine (30 mL), dried (MgSO$_4$), filtered and concentrated. The crude material was purified on silica gel using a 0-2% gradient of EtOAc in hexanes to afford 395 mg (70%/o) of 19 as an oil: IR (neat) 2975, 2929, 1733, 1140 cm$^{-1}$; $^1$H NMR (300 MHz, CDCl$_3$) δ 5.64 (dd, J=17.4, 10.5 Hz, 1H), 4.94 (dd, J=10.6, 1.5 Hz, 1H), 4.83 (dd, J=17.4, 1.5 Hz, 1H), 2.91 (d, J=17.1 Hz, 1H), 2.77 (d, J=16.9 Hz, 1H), 2.09-1.86 (m, 2H), 1.59 (s, 3H), 1.56-1.42 (m, 3H), 1.39 (s, 9H), 1.04 (s, 3H); $^{13}$C NMR (75 MHz, CDCl$_3$) δ 171.95 (s), 146.84 (d), 133.14 (s), 127.81 (s), 112.57 (t), 79.96 (s), 42.16 (s), 37.67 (t), 36.15 (t), 32.52 (t), 28.14 (q), 24.36 (q), 20.51 (q), 18.88 (t); GC-EIMS m/z (% rel. abundance) 250 (1), 194 (78), 149 (10), 133 (35), 107 (28), 57 (100).

2-(2,6-Dimethyl-2-ethenylcyclohex-1-enyl) acetic acid (7): A mixture of 19 (300 mg, 1.19 mmol) and p-TsOH.H$_2$O (31 mg, 0.016 mmol) in CH$_3$CN (4 mL) was warmed at 70° C. After 4 h, the mixture was adsorbed onto silica gel and purified on silica gel eluting with a gradient of 0-25% EtOAc in hexanes to afford 7 (208 mg, 89%) as an off white solid: IR (neat) 3400-2700 (broad), 2930, 1706, 1409 cm$^{-1}$; $^1$H NMR (300 MHz, CDCl$_3$) δ 11.19 (s, 1H), 5.68 (dd, J=17.4, 10.6 Hz, 1H), 5.00 (dd, J=10.5, 1.6 Hz, 1H), 4.88 (dd, J=17.4, 1.6 Hz, 1H), 3.08 (d, J=17.5 Hz, 1H), 2.95 (d, J=17.5 Hz, 1H), 2.11-1.93 (m, 2H), 1.64 (s, 3H), 1.61-1.40 (m, 4H), 1.09 (s, 3H); $^{13}$C NMR (75 MHz, CDCl$_3$) δ 179.51 (s), 146.49 (d), 134.10 (s), 126.84 (s), 112.93 (t), 42.18 (s), 37.55 (t), 34.75 (t), 32.51 (t), 24.29 (q), 20.55 (q), 18.77 (q); $^{13}$C NMR (75 MHz, MeOD$_4$) δ 176.37 (s), 147.78 (d), 134.53 (s), 128.52 (s), 113.24 (t), 43.22 (s), 38.64 (t), 35.43 (t), 33.36 (t), 24.78 (q), 20.54 (q), 19.74 (t); GC-EIMS m/z (% rel. abundance) 194 (46), 179 (52), 166 (12), 133 (85), 119 (100), 107 (47).

Summary: A process for the synthesis of trans-fused γ-lactones having Formula (IV) from substituted cyclic ketones having Formula (I). A diastereoselective synthesis of (±)-epianastrephin (wherein: R$^1$ is ethenyl, R$^2$ and R$^3$ is methyl and n is 1), (±)-anastrephin (wherein: R$^2$ is ethenyl, R$^1$ and R$^3$ is methyl and n is 1), and analogs thereof (wherein: R$^1$ is H, C$_{1-5}$ alkyl, C$_{2-6}$ alkenyl or C$_{2-6}$ alkynyl, R$^2$ is H, C$_{1-5}$ alkyl, C$_{2-6}$ alkenyl or C$_{2-6}$ alkynyl or R$^1$ and R$^2$ together with the carbon atom to which they are attached form a C$_{3-6}$ cycloalkyl ring, R$^3$ is C$_{1-5}$ alkyl and n is 0, 1, or 2):

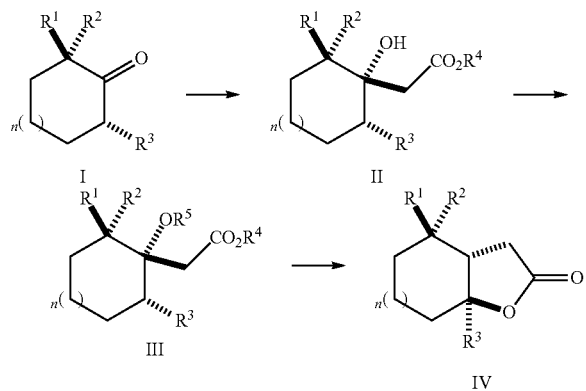

All of the references cited herein, including U.S. patents, are incorporated by reference in their entirety. Also incorporated by reference in their entirety are the following references: Nation, J. L., Ann. Entomol. Soc. Amer., 65: 1364 (1972); Nation, J. L., Environ. Entomol., 4: 27 (1975); Lima, I. S., et al., J. Braz. Chem. Soc., 12: 196 (2001); USDA, APHIS, Fruit Fly Exclusion and Detection Programs 2011, Exotic Fruit Fly Strategic Plan FY2011-2015; Tan, K. H., et al., Pheromones, male lures, and trapping of tephritid fruit flies; and Epsky, N. D., et al., History and development of food-based attractants, IN: Trapping and the detection, control, and regulation of tephritid fruit flies, Shelly. T., et al., Eds., Springer: Dordrecht, 2014, pp. 15-118; Lu, F., and Teal, P. E. A., Arch. Insect Biochem. Physiol., 48: 144 (2001); Walse, S. S., et al., J. Nat. Prod., 71: 1726 (2008); Walse, S. S., et al., Green Chem. Lett. Rev., 1: 205 (2008); Walse, S. S., et al., U.S. Pat. No. 8,128,948. Compositions and Methods for, Attracting Anastrepha Species. June 2008; Battiste, M. A., et al., Tetrahedron Lett., 24: 2611 (1983); Visnick, M., Ph.D. Dissertation, University of Florida, 1983; Strekowski, L., et al., J. Org. Chem., 51: 4836 (1986); Saito, A., et al., Chem. Lett. 729 (1984); Battiste, M. A., et al., Tetrahedron Lett., 32: 5303 (1991); Mori, K., et al., Ann. Chem., 167 (1988); Battiste, M. A., et al., Tetrahedron Lett., 29: 6565 (1988); Vecchio, G. H.-D., and Oehlschlager, A. C., J. Org. Chem., 59: 4853 (1994); Battiste, M. A., et al., J. Org. Chem., 61: 6454 (1996); Wada, K., et al., Synlett., 27A-E (2016); Tadano, K., et al., Tetrahedron Lett., 33: 7899 (1992); Tadano, K., et al., J. Org. Chem., 58: 6266 (1993); Irie, O., and Shishido, K., Chem. Lett., 53 (1995); Schultz, A. G., and Kirincich S. J., J. Org. Chem., 61: 5626 (1996); Strekowski, L., and Battiste, M. A., Tetrahedron Lett., 22: 279 (1981); Nation, J.L., The role of pheromones in the mating system of Anastrepha fruit flies, IN: Fruit flies: their biology, natural enemies and control, Robinson A. S., and Hopper, G., Eds., Elsevier: Amsterdam, 1989, Vol. 3A, pp 189-205; Robacker, D. C., and Hart, W. G., Entomol. Exp. Appl., 39: 103 (1985); Robacker, D. C., et al., Entomol. Exp. Appl., 40: 123 (1986); Matsumoto, T., et al., Bull. Chem. Soc. Jpn., 45: 1147 (1972); Dobrev, A., and Ivanov, C., Synthesis, 8: 562 (1977); Watanabe, S., et al., J. Jpn. Oil Chem. Soc., 29: 43 (1980); Fujitga, T., et al., J. Org. Chem., 49: 1975 (1984); Bunce, R. A., et al., Synthetic Communications, 19: 2423 (1989); Fujita, T., et al., Synthesis, 33: 1846 (2001); Kasashima, Y., et al., J. Oleo Sci., 56: 189 (2007); Yadav J. S., et al., Tetrahedron Lett., 47: 4921 (2006); Siato, A., et al., Chem. Lett., 1065 (1978); Hoye, T. R., and Kurth, M. J., J. Org. Chem., 43: 3693 (1978); Imamura, P. M., and Santiago, G. M. P., Synthetic Communications, 27: 2479 (1997); Chakraborti, A. K., et al., Tetrahedron Lett., 44: 6749 (2003); Karimi, B., Maleki, J., J. Org. Chem., 68: 4951 (2003); Rezaei, H., and Normant, J. F., Synthesis, 32: 109 (2000); Matsumoto, T., et al., Bull. Chem. Soc. Jpn., 45: 1147 (1972); Curini, M., et al., J. Org. Chem., 55: 311 (1990); Tashiro, D., et al., J. Org. Chem., 62: 8141 (1997); Wada, A., et al., Synthesis, 37: 1581 (2005); Clive, D. L. J., et al., J. Org. Chem., 47: 1632 (1982); Arisawa, M., et al., Synthesis, 34: 138 (2002); Jones, I. L., et al., Org. Lett., 11: 5526 (2009); Paterson, I., Tetrahedron, 44: 4207 (1988); Chang, T. C. T., Organic Synthesis, 66: 95 (1988); Jung, M. E., Murakami, M., Org. Lett., 8: 5857 (2006); Baker, J. D., and Heath, R. R., J. Chem. Ecol., 19: 1511 (1993), Hagiwara, H., et al., Tetrahedron, 60: 1983 (2004); Drumright, R. E., and V.L. Taylor, Synthetic Communications, 19: 2423 (1989).

Thus, in view of the above, there is described (in part) the following:

A process of making trans-fused γ-lactones of Formula (IV)

(IV)

wherein:
$R^1$ is H, $C_{1-5}$ alkyl, $C_{2-6}$ alkenyl or $C_{2-6}$ alkynyl,
$R^2$ is H, $C_{1-5}$ alkyl, $C_{2-6}$ alkenyl or $C_{2-6}$ alkynyl,
$R^1$ and $R^2$ together with the carbon atom to which they are attached form a $C_{3-6}$ cycloalkyl ring,
$R^3$ is $C_{1-5}$ alkyl,
n is 0, 1, or 2 to form a 5-, 6- or 7-membered ring,
said process comprising (or consisting essentially of or consisting of):
(a) reacting the cyclic ketone of Formula (I) with an organometallic reagent $MCH_2CO_2R^4$ where M is Li, Na, K, or MgX, where X is Cl, Br, or I, where $R^4$ is $C_{1-4}$ alkyl in a solvent to form the alcohol of Formula (II)

(b) reacting a compound of Formula (II) with a suitable acylation agent (such as acetyl chloride or acetic anhydride), or a suitable chloroformate (such as ethyl chloroformate) in the presence of a suitable catalyst or a suitable base in a suitable solvent, or a suitable acyl transfer reagent in the presence of a suitable acid catalyst and suitable organic catalyst in a suitable solvent to provide a compound of Formula (III) where $R^5$ is $—C(O)C_{1-6}$ alkyl or $—C(O)OC_{1-6}$ alkyl (c) cyclizing the compound of Formula (III) with a suitable organic acid or a suitable Lewis acid in a suitable solvent to form the trans-fused γ-lactone of Formula (IV)

The process above, wherein the solvent of step (a) is selected from the group consisting of THF, $Et_2O$, MTBE, DME, or dioxane, preferably THF.

The process above, wherein the organometallic reagent $(MCH_2CO_2R^4)$ of step (a) is generated from (1) the corresponding neutral acetate precursor with a base selected from lithium diisopropylamide (LDA) or lithium bis(trimethylsilyl)amide (LiHMDS), sodium hexamethyldisilazide (NaHMDS), potassium hexamethyldisilazide (KHMDS), sodium hydride, potassium hydride or from (2) the Grignard reagent generated from the corresponding α-halo ester $(XCH_2CO_2R^4$ where X is Cl, Br, or I) and isopropyl magnesium bromide or magnesium.

The process above, wherein the solvent of step (b) is selected from the group consisting of DCM, acetonitrile, or nitromethane, preferably acetonitrile.

The process above, wherein the catalyst of step (b) is indium (III) chloride, LiOTf or NBS.

The process above, wherein the organic base of step (b) is TEA or Hunig's base.

The process above, wherein the acyl transfer reagent of step (b) is isopropenyl acetate, vinyl acetate or methyl vinyl acetate, preferably isopropenyl acetate.

The process above, wherein the acid catalyst of step (b) is p-TsOH.$H_2O$ or methane sulfonic acid, preferably p-TsOH.$H_2O$.

The process above, wherein the acyl transfer organic catalyst of step (b) is an oxime, preferably cyclohexanone oxime.

The process above, wherein an organic acid of step (c) is p-TsOH.$H_2O$ or $MeSO_3H$, and a Lewis acid complex of step (c) is $BX_3$.L, $GaX_3$.L, or $AlX_3$ where X is F, Cl or Br, and where L is $Et_2O$ or acetonitrile or dimethyl sulfide, preferably p-TsOH.$H_2O$ or $BF_3.Et_2O$.

The process above, wherein a solvent of step (c) is acetonitrile or nitromethane, preferably acetonitrile.

The process above of making diastereoselectively trans-fused γ-lactones of the Formula (IV)

(IV)

wherein:
$R^1$ is H, $C_{1-5}$ alkyl, $C_{2-6}$ alkenyl or $C_{2-6}$ alkynyl,
$R^2$ is H, $C_{1-5}$ alkyl, $C_{2-6}$ alkenyl or $C_{2-6}$ alkynyl,
$R^1$ and $R^2$ are not equal,
$R^3$ is $C_{1-5}$ alkyl,
n is 0, 1, or 2 to form a 5-, 6- or 7-membered ring.

The process above wherein said trans-fused γ-lactone of Formula (IV)

(IV)

is (±)-epianastrephin (2),
wherein:
$R^1$ is ethenyl,
$R^2$ is methyl, $R^3$ is methyl, and n is 1 to form a 6-membered ring, the process comprising (or consisting essentially of or consisting of):

(a) reacting ketone 9 with a suitable base (such as LDA or LiHMDS) followed by zinc chloride and acetaldehyde in a suitable solvent (such as THF) to form the alcohol 10

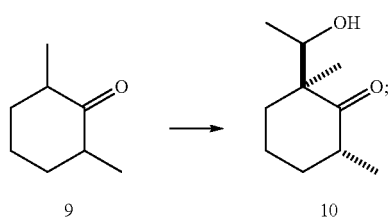

9          10

(b) reacting alcohol 10 with a suitable dehydrating agent in a suitable solvent (such as toluene) to form vinyl ketone 11, or reacting alcohol 10 with a sulfonyl chloride (such as methanesulfonyl chloride or p-TsCl) in a suitable solvent followed by elimination with a suitable base (such as 2,4,6-trimethylpyridine or 1,8-diazabicyclo[5.4.0]undec-7ene) to form vinyl ketone 11

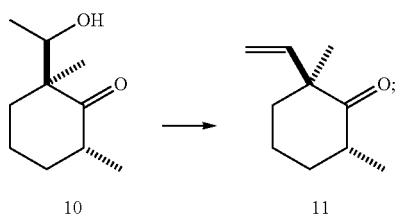

10          11

(c) reacting the vinyl ketone 11 with an acetate anion (generated from preferably t-butyl acetate) and a suitable base (such as LDA or LiHMDS) in a suitable solvent to form the alcohols 12A and 12B

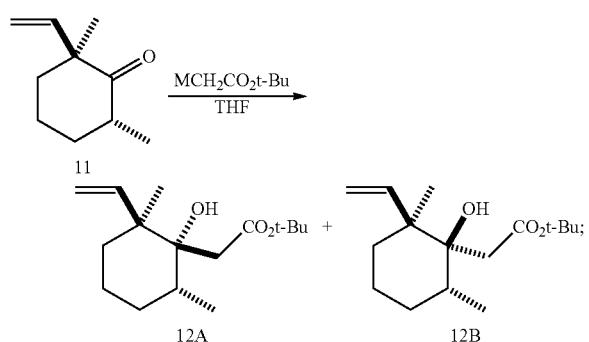

12A          12B (d) reacting alcohol 12A with a suitable acylating agent (such as isopropenyl acetate) in the presence of a suitable acid catalyst (such asp-TsOH.H$_2$O) and cyclohexanone oxime in a suitable solvent (such as acetonitrile) to provide the acylated alcohol 13

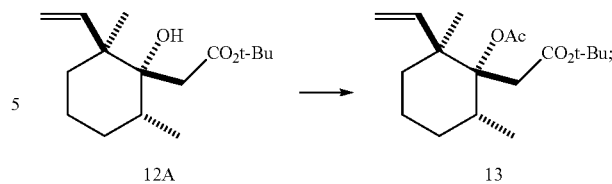

12A          13

(e) cyclizing acylated alcohol 13 with a suitable Lewis acid complex (such as BX$_3$.L, GaX$_3$.L, or AlX$_3$ where X is F, Cl or Br, and where L is Et$_2$O or acetonitrile or dimethyl sulfide), in a suitable solvent (such as acetonitrile) to form the trans-fused γ-lactone, (±)-epianastrephin (1)

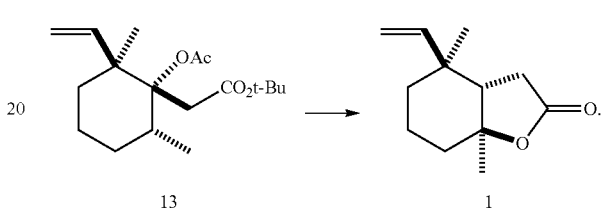

13          1

The process above, wherein the dehydrating agent of step (b) is bis(α,α-bis(trifluoromethyl)benzenemethanolato)diphenylsulfur (Martin's sulfurane), Burgess's reagent, P$_2$O$_5$, SOCl$_2$, preferably Martin's sulfurane.

The process above wherein said trans-fused γ-lactone of Formula (IV)

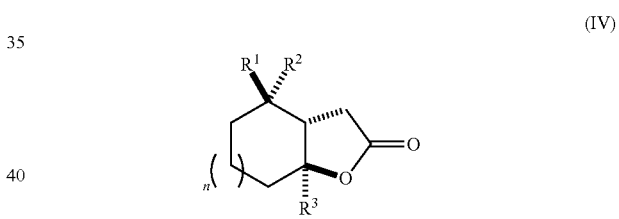

(IV)

is (±)-anastrephin (2), wherein:

$R^1$ is methyl, $R^2$ is ethenyl, $R^3$ is methyl, and n is 1 to form a 6-membered ring, the process comprising (or consisting essentially of or consisting of):

(a) reacting ketone 9 with a suitable silyl chloride (such as TMSCl), a suitable base (such as Et$_3$N and sodium iodine) in a suitable solvent (such as acetonitrile); or reacting ketone 9 with a suitable base (such as LDA, NaHMDS or LHMDS) and a silyl chloride in a suitable solvent (such as THF, ether or DME) to form the silyl enol ether 14

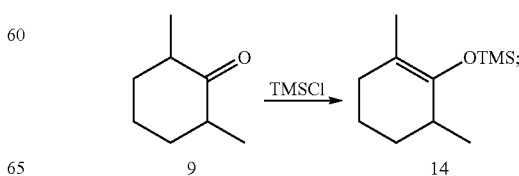

9          14

(b) reacting silyl enol ether 14 with TMSA in the presence of a suitable Lewis acid (such as gallium trichloride) in a suitable solvent (such as pentane or methyl cyclohexane) followed by the addition of THF and a suitable acid (such as sulfuric acid) to form the ketone 15

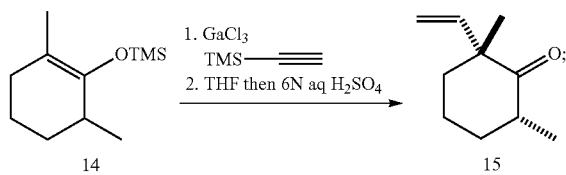

(c) reacting ketone 15 with an acetate anion generated from bromo t-butyl acetate or t-butyl acetate, preferably t-butyl acetate where M is Li, Na, K or MgBr and a suitable base (such as LDA or LiHMDS) in a solvent to form alcohols 16A and 16B

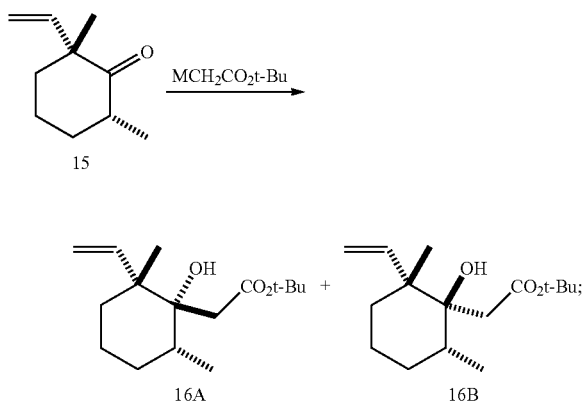

(d) reacting alcohol 16A with a suitable acylating agent (such as isopropenyl acetate) in the presence of a suitable acid catalyst (such asp-TsOH.H₂O) and cyclohexanone oxime in a suitable solvent to provide the acylated alcohol 17

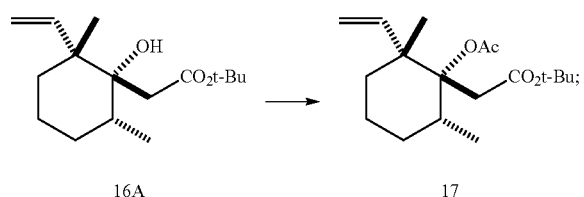 [SMILES: C=C[C@@]1(C)CCC[C@@H](C)[C@]1(O)CC(=O)OC(C)(C)C ; C=C[C@@]1(C)CCC[C@@H](C)[C@@]1(CC(=O)OC(C)(C)C)OC(C)=O]

(e) cyclizing acylated alcohol 17 with a suitable Lewis acid or suitable Lewis acid complex (such as BX₃.L, GaX₃.L, or AlX₃ where X is F, Cl or Br and L is Et₂O or acetonitrile or dimethyl sulfide), in a suitable solvent (such as acetonitrile) to form the trans-fused γ-lactone, (±)-anastrephin (2)

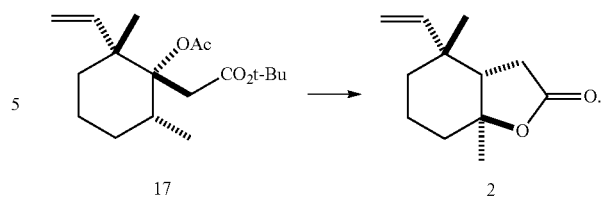

A process of making compound 18, said process comprising (or consisting essentially of or consisting of) hydrogenation of (±)-anastrephin (2) using a suitable catalyst (such as 10% palladium on carbon, Adam's catalyst, Lindlar's catalyst, palladium (II) sulfide or palladium on barium sulfate) in a suitable solvent (such as methanol, ethanol, ethyl acetate or a mixture thereof, preferably ethyl acetate) to form compound 18:

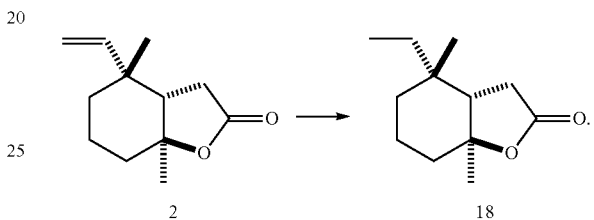

A process of making compound 20, said process comprising (or consisting essentially of or consisting of) hydrogenation of (±)-epianastrephin (1) using a suitable catalyst (such as 10% palladium on carbon, Adam's catalyst, Lindlar's catalyst, palladium (II) sulfide or palladium on barium sulfate) in a suitable solvent (such as methanol, ethanol, ethyl acetate or a mixture thereof, preferably ethyl acetate) to form compound 20:

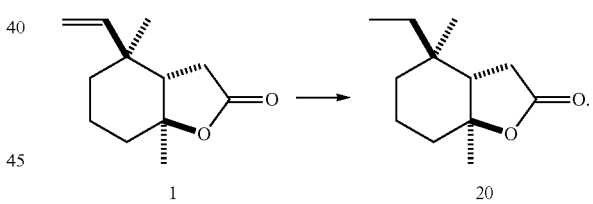

A process of making ketone 11 that may be used to make (±)-epianastrephin (1), said process comprising (or consisting essentially of or consisting of) epimerization of ketone 15 using a suitable acid catalyst (such asp-TsOH.H₂O, trifluoroacetic acid, sulfuric acid) in a suitable solvent (such as toluene or DCM); or using a suitable base (such as LDA, sodium hydride or potassium hydride) in a suitable solvent (such as THF, dioxane or DME) followed by protonation to provide the diastereomeric ketone 11

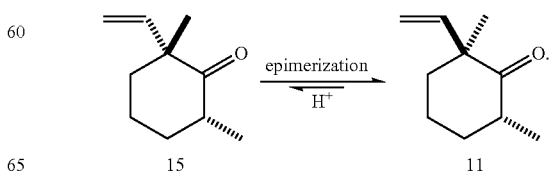

A process of making the aglycon 7 of suspensosides A and B (8) from a compound of Formula (II)

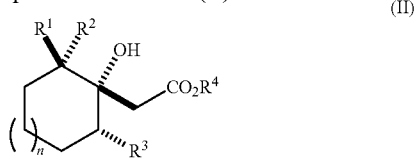

(II)

wherein:
R¹ is ethenyl or methyl,
R² is ethenyl or methyl,
R¹ and R² are not the same,
R³ is methyl,
R⁴ is methyl, ethyl, propyl, t-butyl, and
n is 1 to form a 6-membered ring,
said process by example comprising (or consisting essentially of or consisting of):
(a) dehydrating alcohol 12A with a suitable dehydrating agent in a suitable solvent to provide olefin 19, or reacting alcohol 12A with a sulfonyl chloride (such as methanesulfonyl chloride or p-TsCl) in a suitable solvent followed by elimination with a suitable base (such as 2,4,6-trimethylpyridine or 1,8-diazabicyclo[5.4.0]undec-7ene) to provide olefin 19

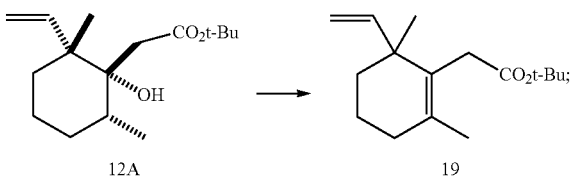 [SMILES: C=C[C@@]1(C)CCC[C@@H](C)[C@]1(O)CC(=O)OC(C)(C)C ; C=CC1(C)CCCC(C)=C1CC(=O)OC(C)(C)C]

12A            19

(b) deprotection of the t-butyl ester of olefin 19 with a suitable acid (such as p-toluene sulfonic acid or trifluoroacetic acid) in a suitable solvent to provide aglycon 7 of suspensosides A and B (8)

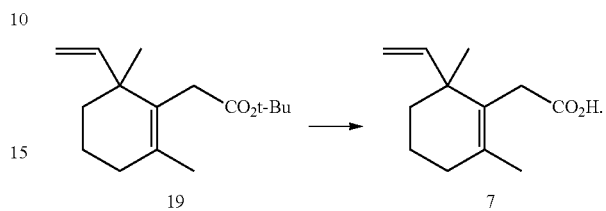

19            7

The process above, wherein the dehydrating agent of step (a) is $SOCl_2$, bis(α,α-bis(trifluoromethyl)benzenemethanolato)diphenylsulfur (Martin's sulfurane), Burgess's reagent or $P_2O_5$, preferably $SOCl_2$.

The process above, wherein a solvent of step (a) is pyridine, toluene, DCM, THF or dioxane, preferably pyridine.

The process above, wherein a solvent of step (b) is toluene, DCM or acetonitrile, preferably acetonitrile.

A compound in the table below which may be used to make (±)-epianastrephin (1), said compound having the relative stereochemistry depicted in the table below:

| Structure | Name | Data[a] |
|---|---|---|
| 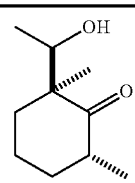 | 2-(1-Hydroxyethyl)-2,6-dimethylcyclohexanone | $^{13}C$ NMR (75 MHz, $CDCl_3$) δ 221.13 (q), 71.59 (d), 52.10 (q), 41.40 (d), 37.09 (t), 36.49 (t), 21.11 (t), 15.86 (s), 15.81 (s), 14.67 (s); minor diastereomer δ 216.81 (q), 69.95 (d), 53.28 (q), 41.31 (d), 37.53 (t), 35.81 (t), 20.53 (t), 17.39 (s), 16.05 (s), 15.19 (s) |
| 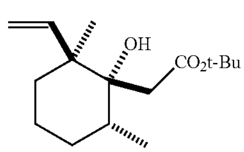 | tert-Butyl 1-((1R*,2S*,6R*)-1-hydroxy-2,6-dimethyl-2-ethenylcyclohexyl) acetate | IR (neat) 3447 (broad), 2929, 1700, 1147 cm−1; 1H NMR (300 MHz, CDCl3) δ 6.19 (ddd, J = 17.3, 11.2, 1.1 Hz, 1H), 5.14-5.00 (m, 2H), 2.44 (dd, J = 16.2, 1.1 Hz, 1H), 2.17 (dd, J = 16.1, 1.1 Hz, 1H), 1.92-1.75 (m, 1H), 1.75-1.54 (m, 1H), 1.45 (s, 6H), 1.61-1.37 (m, 4H), 1.33 (s, 1H), 1.30-1.18 (m, 1H), 1.06 (d, J = 1.1 Hz, 3H), 0.86 (dd, J = 6.4, 1.1 Hz, 3H); 13C NMR 75 MHz, CDCl3) δ 174.83 (q), 142.64 (d), 113.90 (t), 81.62 (q), 75.19 (q), 45.60 (q), 38.15 (t), 38.09 (d), 35.17 (t), 30.49 (t), 28.01 (s), 21.67 (s), 21.47 (t), 16.67 (s); GC-EIMS m/z (% rel. abundance) 212 (9), 194 (31), 96 (100) |
| 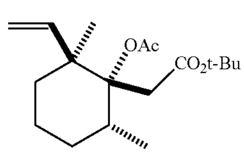 | tert-Butyl 1-((1R*,2S*,6R*)-1-acetoxy-2,6-dimethyl-2-ethenylcyclohexyl) acetate | IR (neat) 2976, 2933, 1734, 1151 cm⁻¹; ¹H NMR (300 MHz, $CDCl_3$) δ 6.20 (dd, J = 17.5, 11.0 Hz, 1H), 5.50-4.81 (m, 2H), 3.17 (s, 2H), 2.44 (q, J = 6.9 Hz, 1H), 2.08 (s, 3H), 1.77 (ddd, J = 12.8, 11.1, 4.3 Hz, 1H), 1.57-1.43 (m, 3H), 1.39 (s, 9H), 1.12 (s, 3H), 1.03 (d, J = 6.8 Hz, 3H); $^{13}C$ NMR (75 MHz, $CDCl_3$) δ 170.61 (q), 169.86 (q), 142.30 (d), 114.17 (t), 88.51 (q), 79.97 (q), 46.01 (q), 37.26 (t), 36.25 (d), 35.75 (t), 30.16 (t), 28.02 (s), 22.98 (s), 22.53 (s), 20.40 (t), 17.95 (s); GC-EIMS m/z (% rel. abundance) 254 (3), 236 (7), 194 (62), 138 (59), 57 (100) |

A compound in the table below which may be used to make (±)-anastrephin (2), said compound having the relative stereochemistry depicted in the table below:

| Structure | Name | Data[a] |
|---|---|---|
| [structure] | tert-Butyl 1-((1R*,2R*,6R*)-1-hydroxy-2,6-dimethyl-2-ethenylcyclohexyl) acetate | IR (neat) 3443 (broad), 2977, 2933, 1699, 1149 cm$^{-1}$; $^1$H NMR (300 MHz, CDCl$_3$) δ 6.28 (dd, J = 17.7, 11.0 Hz, 1H), 5.10-4.94 (m, 2H), 2.46 (d, J = 15.9 Hz, 1H), 2.17 (d, J = 15.9, 1.0 Hz, 1H), 2.08-1.87 (m, 1H), 1.81-1.68 (m, 1H), 1.43 (s, 9H), 1.31 (s, 1H), 1.03 (s, 3H), 0.84 (d, J = 6.6, 3H); $^{13}$C NMR (75 MHz, CDCl$_3$) δ 174.64 (q), 146.49 (d), 112.75 (q), 81.65 (q), 75.33 (q), 45.28 (q), 38.78 (t), 37.22 (d), 34.43 (t), 30.53 (t), 28.05 (s), 21.50 (t), 17.91 (s), 16.74 (s); GC-EIMS m/z (% rel. abundance) 212 (14), 194 (42), 96 (100) |
| [structure] | tert-Butyl 1-((1R*,2R*,6R*)-1-acetoxy-2,6-dimethyl-2-ethenylcyclohexyl) acetate | IR (neat) 2976, 2935, 1730, 1149 cm$^{-1}$; $^1$H NMR (300 MHz, CDCl$_3$) δ 6.12 (dd, J = 17.6, 11.0 Hz, 1H), 5.02 (ddd, J = 17.8, 11.2, 1.6 Hz, 2H), 3.32 (d, J = 15.9 Hz, 1H), 3.17 (d, J = 15.9 Hz, 1H), 2.46-2.31 (m, 1H), 2.06 (s, 3H), 1.90 (m, 1H), 1.57-1.45 (m, 1H), 1.41 (s, 9H), 1.21-1.12 (m, 1H), 1.11 (s, 3H), 1.01 (d, J = 6.8 Hz, 3H); $^{13}$C NMR (75 MHz, CDCl$_3$) δ 170.55 (q), 169.94 (q), 145.02 (d), 112.40 (t), 89.06 (q), 80.17 (q), 45.68 (q), 37.51 (t), 35.88 (d), 35.00 (t), 30.31 (t), 28.04 (s), 22.62 (s), 20.97 (s), 20.45 (t), 17.94 (s) |

The compound in the table below, said compound having the relative stereochemistry depicted in the table below:

| Structure | Name | Data[a] |
|---|---|---|
| [structure] | (3aS*,4S*,7aS*)-4,7a-Dimethyl-4-ethylhexahydrobenzofuran-2(3H)-one | IR (neat) 2939, 2871, 1770, 1028, 954, 928 cm$^{-1}$; $^1$H NMR (300 MHz, CDCl$_3$) δ 2.49 (dd, J = 16.3, 14.9 Hz, 1H), 2.31 (dd, J = 16.3, 6.5 Hz, 1H), 2.15-1.90 (m, 2H), 1.85-1.69 (m, 2H), 1.68-1.40 (m, 3H), 1.36 (s, 3H), 1.33-1.24 (m, 1H), 1.19-0.97 (m, 1H), 0.91 (s, 3H), 0.85 (t, J = 7.5 Hz, 3H), $^{13}$C NMR (75 MHz, CDCl$_3$) δ 176.62 (s), 86.57 (s), 56.81 (d), 37.68 (t), 36.36 (t), 35.68 (s), 29.40 (t), 27.64 (q), 24.44 (t), 21.08 (q), 20.53 (t), 9.05 (q), GC-EIMS m/z (% rel. abundance) 181 (70), 167 (37), 153 (73), 139 (25), 81 (93), 55 (100) |

The compound in the table below that may be used to make analogs of (±)-epianastrephin (1) and (±)-anastrephin (2), said compound having the relative stereochemistry depicted in the table below:

| Structure | Name | Data[a] |
|---|---|---|
| [structure] | tert-Butyl 1-((1R*,6R*)-1-acetoxy-2,2,6-trimethylcyclohexyl) acetate | IR (neat) 2976, 2932, 1729, 1148 cm$^{-1}$; $^1$H NMR (300 MHz, Chloroform-d) δ 3.34 (d, J = 15.8 Hz, 1H), 3.21 (d, J = 15.8 Hz, 1H), 2.42-2.24 (m, 1H), 2.05 (s, 3H), 1.78-1.63 (m, 1H), 1.55-1.39 (m, partially obscured by singlet at 1.42 ppm, 4H), 1.42 (s, 9H), 1.18-1.05 (m, 1H), 1.03 (d, partially obscured by singlets at 1.00 ppm, J = 6.6 Hz, 3H), 1.00 (s, 6H); $^{13}$C NMR (75 MHz, CDCl$_3$) δ 170.78 (s), 170.28 (s), 90.32 (s), 80.18 (s), 40.52 (s), 37.81 (t), 37.03 (t), 35.75 (d), 30.63 (t), 28.01 (q), 27.08 (q), 24.26 (q), 22.64 (q), 21.15 (t), 18.15 (q) |

The term "consisting essentially of" excludes additional method (or process) steps or composition components that substantially interfere with the intended activity of the method (or process) or composition, and can be readily determined by those skilled in the art (for example, from a consideration of this specification or practice of the invention disclosed herein).

The invention illustratively disclosed herein suitably may be practiced in the absence of any element (e.g., method (or process) steps or composition components) which is not specifically disclosed herein.

Unless otherwise indicated, all numbers expressing quantities of ingredients, properties such as molecular weight, reaction conditions (e.g., reaction time, temperature), percentages and so forth as used in the specification and claims are to be understood as being modified in all instances by the term "about." Accordingly, unless otherwise indicated, the numerical properties set forth in the following specification and claims are approximations that may vary depending on the desired properties sought to be obtained in embodiments of the present invention. As used herein, the term "about" refers to a quantity, level, value, or amount that varies by as much as 10% to a reference quantity, level, value, or amount.

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described.

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

TABLE 1

| Structure | Name | Data[a] |
|---|---|---|
| (structure) | 2-(1-Hydroxyethyl)-2,6-dimethylcyclohexanone | $^{13}$C NMR (75 MHz, CDCl$_3$) δ 221.13 (q), 71.59 (d), 52.10 (q), 41.40 (d), 37.09 (t), 36.49 (t), 21.11 (t), 15.86 (s), 15.81 (s), 14.67 (s); minor diastereomer δ 216.81 (q), 69.95 (d), 53.28 (q), 41.31 (d), 37.53 (t), 35.81 (t), 20.53 (t), 17.39 (s), 16.05 (s), 15.19 (s) |
| (structure) | tert-Butyl 1-((1R*,2S*,6R*)-1-hydroxy-2,6-dimethyl-2-ethenylcyclohexyl) acetate | IR (neat) 3447 (broad), 2929, 1700, 1147 cm−1; 1H NMR (300 MHz, CDCl3) δ 6.19 (ddd, J = 17.3, 11.2, 1.1 Hz, 1H), 5.14-5.00 (m, 2H), 2.44 (dd, J = 16.2, 1.1 Hz, 1H), 2.17 (dd, J = 16.1, 1.1 Hz, 1H), 1.92-1.75 (m, 1H), 1.75-1.54 (m, 1H), 1.45 (s, 6H), 1.61-1.37 (m, 4H), 1.33 (s, 1H), 1.30-1.18 (m, 1H), 1.06 (d, J = 1.1 Hz, 3H), 0.86 (dd, J = 6.4, 1.1 Hz, 3H); 13C NMR (75 MHz, CDCl3) δ 174.83 (q), 142.64 (d), 113.90 (t), 81.62 (q), 75.19 (q), 45.60 (q), 38.15 (t), 38.09 (d), 35.17 (t), 30.49 (t), 28.01 (s), 21.67 (s), 21.47 (t), 16.67 (s); GC-EIMS m/z (% rel. abundance) 212 (9), 194 (31), 96 (100) |
| (structure) | tert-Butyl 1-((1R*,2S*,6R*)-1-acetoxy-2,6-dimethyl-2-ethenylcyclohexyl) acetate | IR (neat) 2976, 2933, 1734, 1151 cm$^{-1}$; $^1$H NMR (300 MHz, CDCl$_3$) δ 6.20 (dd, J = 17.5, 11.0 Hz, 1H), 5.50-4.81 (m, 2H), 3.17 (s, 2H), 2.44 (q, J = 6.9 Hz, 1H), 2.08 (s, 3H), 1.77 (ddd, J = 12.8, 11.1, 4.3 Hz, 1H), 1.57-1.43 (m, 3H), 1.39 (s, 9H), 1.12 (s, 3H), 1.03 (d, J = 6.8 Hz, 3H); $^{13}$C NMR (75 MHz, CDCl$_3$) δ 170.61 (q), 169.86 (q), 142.30 (d), 114.17 (t), 88.51 (q), 79.97 (q), 46.01 (q), 37.26 (t), 36.25 (d), 35.75 (t), 30.16 (t), 28.02 (s), 22.98 (s), 22.53 (s), 20.40 (t), 17.95 (s); GC-EIMS m/z (% rel. abundance) 254 (3), 236 (7), 194 (62), 138 (59), 57 (100) |
| (structure) | tert-Butyl 1-((1R*,2R*,6R*)-1-hydroxy-2,6-dimethyl-2-ethenylcyclohexyl) acetate | IR (neat) 3443 (broad), 2977, 2933, 1699, 1149 cm$^{-1}$; $^1$H NMR (300 MHz, CDCl$_3$) δ 6.28 (dd, J = 17.7, 11.0 Hz, 1H), 5.10-4.94 (m, 2H), 2.46 (d, J = 15.9 Hz, 1H), 2.17 (d, J = 15.9, 1.0 Hz, 1H), 2.08-1.87 (m, 1H), 1.81-1.68 (m, 1H), 1.43 (s, 9H), 1.31 (s, 1H), 1.03 (s, 3H), 0.84 (d, J = 6.6, 3H); $^{13}$C NMR (75 MHz, CDCl$_3$) δ 174.64 (q), 146.49 (d), 112.75 (q), 81.65 (q), 75.33 (q), 45.28 (q), 38.78 (t), 37.22 (d), 34.43 (t), 30.53 (t), 28.05 (s), 21.50 (t), 17.91 (s), 16.74 (s); GC-EIMS m/z (% rel. abundance) 212 (14), 194 (42), 96 (100) |
| (structure) | tert-Butyl 1-((1R*,2R*,6R*)-1-acetoxy-2,6-dimethyl-2-ethenylcyclohexyl) acetate | IR (neat) 2976, 2935, 1730, 1149 cm$^{-1}$; $^1$H NMR (300 MHz, CDCl$_3$) δ 6.12 (dd, J = 17.6, 11.0 Hz, 1H), 5.02 (ddd, J = 17.8, 11.2, 1.6 Hz, 2H), 3.32 (d, J = 15.9 Hz, 1H), 3.17 (d, J = 15.9 Hz, 1H), 2.46-2.31 (m, 1H), 2.06 (s, 3H), 1.90 (m, 1H), 1.57-1.45 (m, 1H), 1.41 (s, 9H), 1.21-1.12 (m, 1H), 1.11 (s, 3H), 1.01 (d, J = 6.8 Hz, 3H); $^{13}$C NMR (75 MHz, CDCl$_3$) δ 170.55 (q), 169.94 (q), 145.02 (d), 112.40 (t), 89.06 (q), 80.17 (q), 45.68 (q), 37.51 (t), 35.88 (d), 35.00 (t), 30.31 (t), 28.04 (s), 22.62 (s), 20.97 (s), 20.45 (t), 17.94 (s) |

TABLE 1-continued

| Structure | Name | Data[a] |
|---|---|---|
| 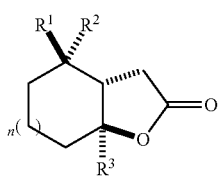 | (3aS*,4S*,7aS*)-4,7a-Dimethyl-4-ethylhexahydrobenzofuran-2(3H)-one | IR (neat) 2939, 2871, 1770, 1028, 954, 928 cm$^{-1}$; $^1$H NMR (300 MHz, CDCl$_3$) δ 2.49 (dd, J = 16.3, 14.9 Hz, 1H), 2.31 (dd, J = 16.3, 6.5 Hz, 1H), 2.15-1.90 (m, 2H), 1.85-1.69 (m, 2H), 1.68-1.40 (m, 3H), 1.36 (s, 3H), 1.33-1.24 (m, 1H), 1.19-0.97 (m, 1H), 0.91 (s, 3H), 0.85 (t, J = 7.5 Hz, 3H), $^{13}$C NMR (75 MHz, CDCl$_3$) δ 176.62 (s), 86.57 (s), 56.81 (d), 37.68 (t), 36.36 (t), 35.68 (s), 29.40 (t), 27.64 (q), 24.44 (t), 21.08 (q), 20.53 (t), 9.05 (q), GC-EIMS m/z (% rel. abundance) 181 (70), 167 (37), 153 (73), 139 (25), 81 (93), 55 (100) |
| 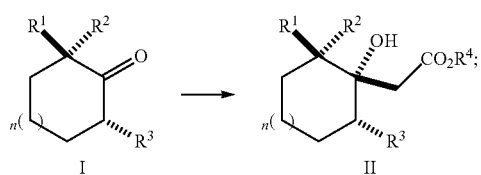 | tert-Butyl 1-((1R*,6R*)-1-acetoxy-2,2,6-trimethylcyclohexyl) acetate | IR (neat) 2976, 2932, 1729, 1148 cm$^{-1}$; $^1$H NMR (300 MHz, CDCl$_3$) δ 3.34 (d, J = 15.8 Hz, 1H, 3.21 (d, J = 15.8 Hz, 1H), 2.42-2.24 (m, 1H), 2.05 (s, 3H), 1.78-1.63 (m, 1H), 1.55-1.39 (m, partially obscured by singlet at 1.42 ppm, 4H), 1.42 (s, 9H), 1.18-1.05 (m, 1H), 1.03 (d, partially obscured by singlets at 1.00 ppm, J = 6.6 Hz, 3H), 1.00 (s, 6H); $^{13}$C NMR (75 MHz, CDCl$_3$) δ 170.78 (s), 170.28 (s), 90.32 (s), 80.18 (s), 40.52 (s), 37.81 (t), 37.03 (t), 35.75 (d), 30.63 (t), 28.01 (q), 27.08 (q), 24.26 (q), 22.64 (q), 21.15 (t), 18.15 (q) |

[a]See Synthetic Examples Section for m.p., IR, NMR, GC-MS instrumentation and methods

We claim:

1. A process of making trans-fused γ-lactones of the Formula (IV)

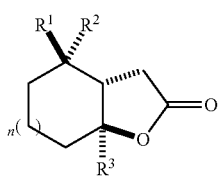

(IV)

wherein:
$R^1$ is H, $C_{1-5}$ alkyl, $C_{2-6}$ alkenyl or $C_{2-6}$ alkynyl,
$R^2$ is H, $C_{1-5}$ alkyl, $C_{2-6}$ alkenyl or $C_{2-6}$ alkynyl,
$R^1$ and $R^2$ together with the carbon atom to which they are attached form a $C_{3-6}$ cycloalkyl ring,
$R^3$ is $C_{1-5}$ alkyl,
n is 0, 1 or 2 to form a 5-, 6- or 7-membered ring, said process comprising:

(a) reacting the cyclic ketone of Formula (I) with an organometallic reagent MCH$_2$CO$_2$R$^4$ where M is Li, Na, K, or MgX, where X is Cl, Br or I, where is $R^4$ is $C_{1-4}$ alkyl, in a solvent to form the alcohol of Formula (II)

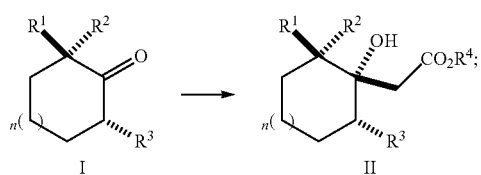

(b) reacting the alcohol of Formula (II) with an acylating agent, or a chloroformate in the presence of a catalyst or a base in a solvent, or an acyl transfer reagent in the presence of an acid catalyst and organic catalyst in a solvent, to provide a compound of Formula (III) where $R^5$ is —C(O)C$_{1-6}$ alkyl or —C(O)OC$_{1-6}$ alkyl

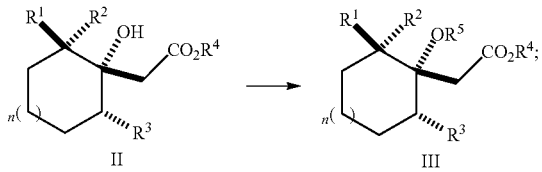

(c) cyclizing the compound of Formula (III) with an organic acid or a Lewis acid in a solvent to form the trans-fused γ-lactone of Formula (IV)

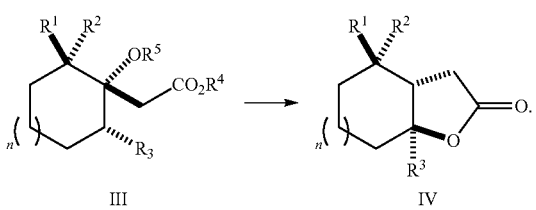

2. The process according to claim 1, wherein the solvent of step (a) is selected from the group consisting of THF, Et$_2$O, MTBE, DME or dioxane.

3. The process according to claim 1, wherein the organometallic reagent (MCH$_2$CO$_2$R$^4$) of step (a) is generated from (1) the corresponding neutral acetate precursor with a base selected from the group consisting of LDA or LiHMDS, NaHMDS, KHMDS, sodium hydride, potassium hydride, or from (2) the Grignard reagent generated from the corresponding α-halo ester XCH$_2$CO$_2$R$^4$ where X is Cl, Br or I and isopropyl magnesium bromide or magnesium.

4. The process according to claim 1, wherein the solvent of step (b) is selected from the group consisting of DCM, acetonitrile or nitromethane.

5. The process according to claim 1, wherein the catalyst of step (b) is selected from the group consisting of indium (III) chloride, LiOTf or NBS.

6. The process according to claim 1, wherein the organic base of step (b) is selected from the group consisting of Et$_3$N or Hunig's base.

7. The process according to claim 1, wherein the acyl transfer reagent of step (b) is selected from the group consisting of isopropenyl acetate, vinyl acetate or methyl vinyl acetate.

8. The process according to claim 1, wherein the acid catalyst of step (b) is selected from the group consisting of p-TsOH.H$_2$O or methane sulfonic acid.

9. The process according to claim 1, wherein the acyl transfer organic catalyst of step (b) is an oxime.

10. The process according to claim 1, wherein the organic acid of step (c) is selected from the group consisting of p-TsOH.H$_2$O or MeSO$_3$H, and a Lewis acid complex of step (c) is selected from the group consisting of BX$_3$.L, GaX$_3$.L or AlX$_3$ where X is F, Cl or Br, and where L is Et$_2$O or acetonitrile or dimethyl sulfide.

11. The process according to claim 1, wherein a solvent of step (c) is selected from the group consisting of acetonitrile or nitromethane.

12. The process according to claim 1 of making diastereoselectively trans-fused γ-lactones of the Formula (IV)

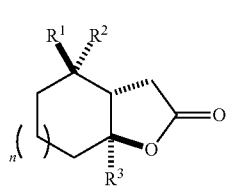

wherein:
R$^1$ is H, C$_{1-5}$ alkyl, C$_{2-6}$ alkenyl or C$_{2-6}$ alkynyl,
R$^2$ is H, C$_{1-5}$ alkyl, C$_{2-6}$ alkenyl or C$_{2-6}$ alkynyl,
R$^1$ and R$^2$ are not equal,
R$^3$ is C$_{1-5}$ alkyl,
n is 0, 1 or 2 to form a 5-, 6- or 7-membered ring.

13. The process according to claim 1 wherein said trans-fused γ-lactone of Formula (IV)

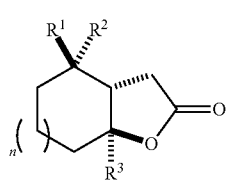

is (±)-epianastrephin (2),
wherein:
R$^1$ is ethenyl,
R$^2$ is methyl,
R$^3$ is methyl, and
n is 1 to form a 6-membered ring,
said process comprising:
(a) reacting ketone 9 with a base followed by zinc chloride and acetaldehyde in a solvent to form alcohol 10

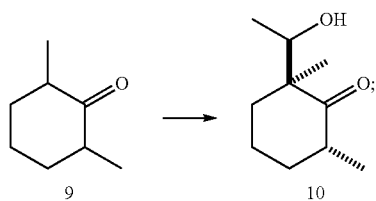

(b) reacting alcohol 10 with a dehydrating agent in a solvent to form the vinyl ketone 11, or reacting alcohol 10 with a sulfonyl chloride followed by elimination with a base to form the vinyl ketone 11

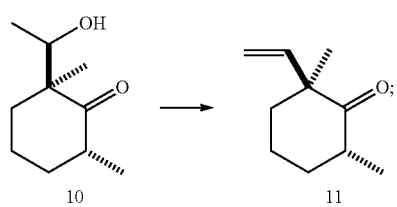

(c) reacting ketone 11 with an organometallic reagent MCH$_2$CO$_2$R$^4$ where M is Li, Na, K or MgX, where X is Cl, Br or I, where R$^4$ is t-butyl in a solvent to form alcohols 12A and 12B

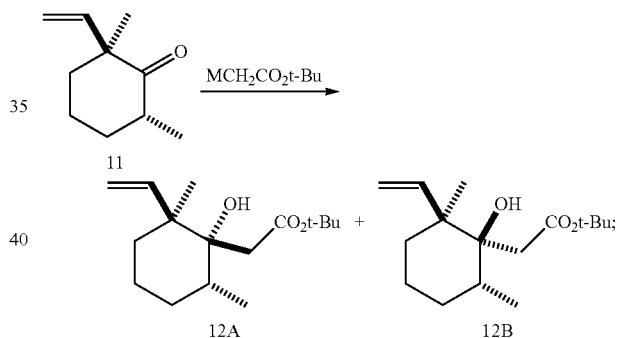

(d) reacting alcohol 12A with an acylating agent in the presence of an acid catalyst in a solvent to provide the acylated alcohol 13

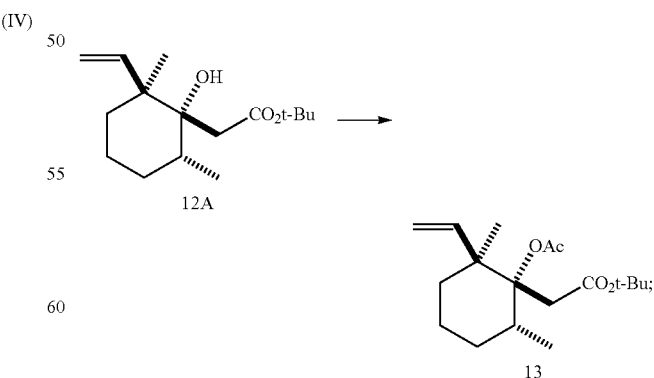

(e) cyclizing compound 13 with a Lewis acid complex in a solvent to form the trans-fused γ-lactone, (±)-epianastrephin (1)

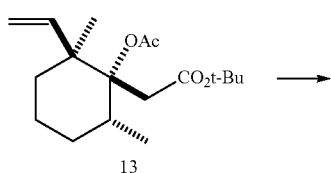

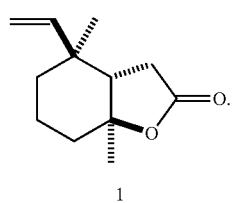

14. The process according to claim 13, wherein the dehydrating agent of step (b) is selected from the group consisting of Martin's sulfurane, Burgess's reagent, $P_2O_5$ or $SOCl_2$.

15. The process according to claim 1 wherein said trans-fused γ-lactone of Formula (IV)

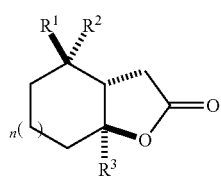

is (±)-anastrephin (2),
wherein:
$R^1$ is methyl,
$R^2$ is ethenyl,
$R^3$ is methyl, and
n is 1 to form a 6-membered ring,
said process comprising:
(a) reacting ketone 9 with a silyl chloride, a base and sodium iodine in a solvent to form the silyl enol ether 14; or reacting ketone 9 with a base and a silyl chloride in a solvent to form the silyl enol ether 14

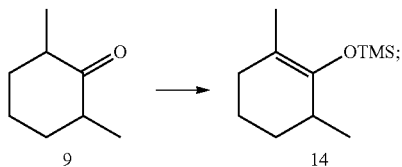

(b) reacting silyl enol ether 14 with TMSA in the presence of a Lewis acid in a solvent followed by the addition of THF and an acid to form the ketone 15

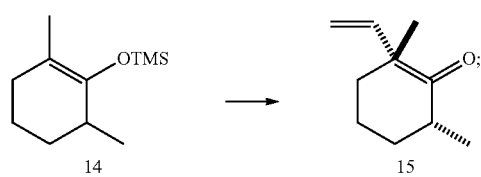

(c) reacting ketone 15 with an organometallic reagent $MCH_2CO_2R^4$ where M is Li, Na, K or MgX, where X is Cl, Br or I, where $R^4$ is t-butyl in a solvent to form alcohols 16A and 16B

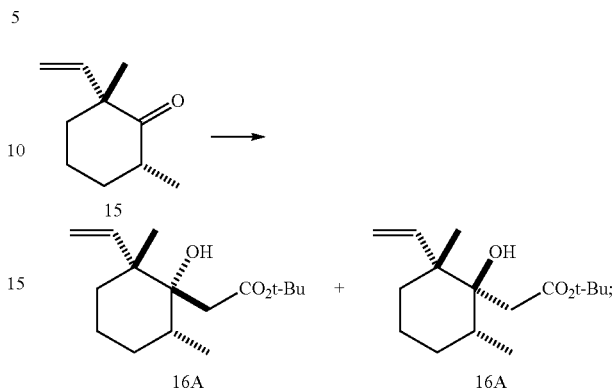

(d) reacting alcohol 16A with an acylating agent in the presence of an acid catalyst and cyclohexanone oxime in a solvent to provide acylated alcohol 17

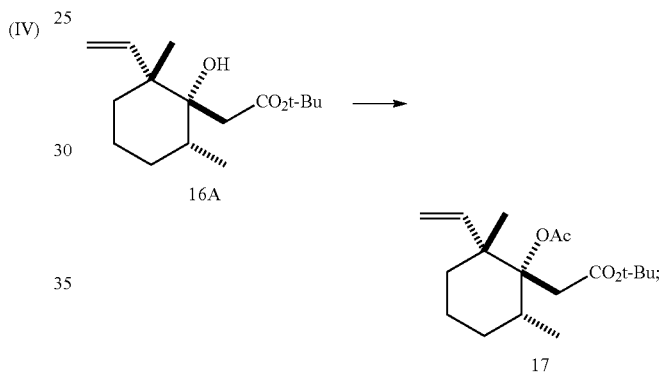

(e) cyclizing compound 17 with a Lewis acid or Lewis acid complex in a solvent to form the trans-fused γ-lactone, (±)-anastrephin (2)

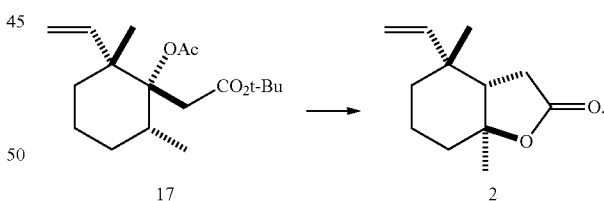

16. A process of making compound 18, said process comprising hydrogenation of (±)-anastrephin (2) using a catalyst in a solvent to form compound 18:

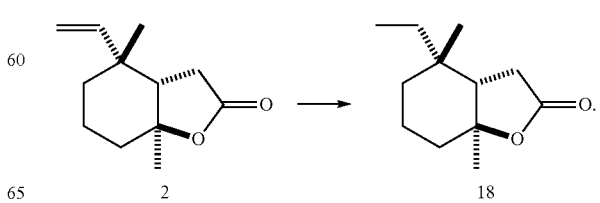

17. A process of making the compound 20, said process comprising hydrogenation of (±)-epianastrephin (1) using a catalyst in a solvent to form the compound 20:

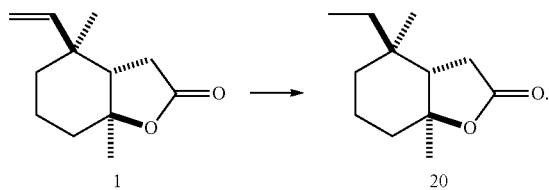

18. A process of making ketone 11 that may be used to make (±)-epianastrephin (1), said process comprising epimerization of ketone 15 using an acid catalyst in a solvent to provide the diastereomeric ketone 11; or using a base in a solvent followed by protonation to provide the diastereomeric ketone 11:

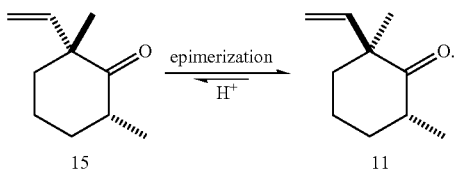

19. A process of making the aglycon 7 of suspensosides A and B (8) from an alcohol of Formula (II)

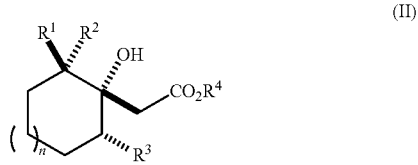

wherein:
$R^1$ is ethenyl or methyl,
$R^2$ is ethenyl or methyl,
$R^1$ and $R^2$ are not the same,
$R^3$ is methyl,
$R^4$ is methyl, ethyl, propyl, t-butyl, and
n is 1 to form a 6-membered ring,
said process comprising:
(a) dehydrating alcohol 12A with a dehydrating agent in a solvent to provide olefin 19, or reacting alcohol 12A with sulfonyl chloride followed by elimination with a base to provide the olefin 19

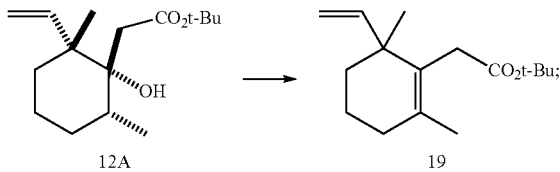 [SMILES: C=C[C@@]1(C)CCC[C@@H](C)[C@]1(O)CC(=O)OC(C)(C)C ; C=CC1(C)CCCC(C)=C1CC(=O)OC(C)(C)C]

(b) deprotection of the t-butyl ester of compound 19 with an acid in a solvent to provide the aglycon 7 of suspensosides A and B (8)

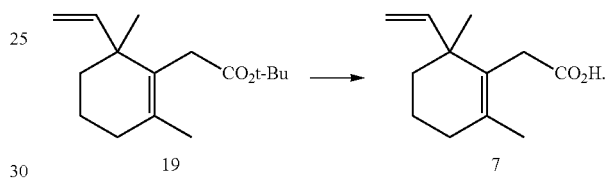

20. The process according to claim 19, wherein the dehydrating agent of step (a) is selected from the group consisting of $SOCl_2$, Martin's sulfurane, Burgess's reagent or $P_2O_5$.

21. The process according to claim 19, wherein the solvent of step (a) is selected from the group consisting of pyridine, toluene, dichloromethane, THF or dioxane.

22. The process according to claim 19, wherein the solvent of step (b) is selected from the group consisting of toluene, DCM or acetonitrile.

23. A compound in the table below which may be used to make (±)-epianastrephin (1), said compound having the relative stereochemistry depicted in the table below:

| Structure | Name | Data[a] |
|---|---|---|
| ![structure] | 2-(1-Hydroxyethyl)-2,6-dimethylcyclohexanone | $^{13}C$ NMR (75 MHz, $CDCl_3$) δ 221.13 (q), 71.59 (d), 52.10 (q), 41.40 (d), 37.09 (t), 36.49 (t), 21.11 (t), 15.86 (s), 15.81 (s), 14.67 (s); minor diastereomer δ 216.81 (q), 69.95 (d), 53.28 (q), 41.31 (d), 37.53 (t), 35.81 (t), 20.53 (t), 17.39 (s), 16.05 (s), 15.19 (s) |
| ![structure] | tert-Butyl 1-((1R*,2S*,6R*)-1-hydroxy-2,6-dimethyl-2-ethenylcyclohexyl) acetate | IR (neat) 3447 (broad), 2929, 1700, 1147 cm−1; 1H NMR (300 MHz, $CDCl_3$) δ 6.19 (ddd, J = 17.3, 11.2, 1.1 Hz, 1H), 5.14-5.00 (m, 2H), 2.44 (dd, J = 16.2, 1.1 Hz, 1H), 2.17 (dd, J = 16.1, 1.1 Hz, 1H), 1.92-1.75 (m, 1H), 1.75-1.54 (m, 1H), 1.45 (s, 6H), 1.61-1.37 (m, 4H), 1.33 (s, 1H), 1.30-1.18 (m, 1H), 1.06 (d, J = 1.1 Hz, 3H), 0.86 (dd, J = 6.4, 1.1 Hz, 3H); 13C NMR (75 MHz, CDCl3) δ 174.83 (q), 142.64 (d), 113.90 (t), 81.62 (q), 75.19 (q), 45.60 (q), 38.15 (t), 38.09 (d), 35.17 (t), 30.49 (t), 28.01 (s), 21.67 (s), 21.47 (t), 16.67 (s); GC-EIMS m/z (% rel. abundance) 212 (9), 194 (31), 96 (100) |

| Structure | Name | Data[a] |
|---|---|---|
| (structure: tert-butyl cyclohexyl with vinyl, OAc, CO₂t-Bu, methyl groups) | tert-Butyl 1-((1R*,2S*,6R*)-1-acetoxy-2,6-dimethyl-2-ethenylcyclohexyl) acetate | IR (neat) 2976, 2933, 1734, 1151 cm$^{-1}$; $^1$H NMR (300 MHz, CDCl$_3$) δ 6.20 (dd, J = 17.5, 11.0 Hz, 1H), 5.50-4.81 (m, 2H), 3.17 (s, 2H), 2.44 (q, J = 6.9 Hz, 1H), 2.08 (s, 3H), 1.77 (ddd, J = 12.8, 11.1, 4.3 Hz, 1H), 1.57-1.43 (m, 3H), 1.39 (s, 9H), 1.12 (s, 3H), 1.03 (d, J = 6.8 Hz, 3H); $^{13}$C NMR (75 MHz, CDCl$_3$) δ 170.61 (q), 169.86 (q), 142.30 (d), 114.17 (t), 88.51 (q), 79.97 (q), 46.01 (q), 37.26 (t), 36.25 (d), 35.75 (t), 30.16 (t), 28.02 (s), 22.98 (s), 22.53 (s), 20.40 (t), 17.95 (s); GC-EIMS m/z (% rel. abundance) 254 (3), 236 (7), 194 (62), 138 (59), 57 (100). |

24. A compound in the table below which may be used to make (±)-anastrephin (2), said compound having the relative stereochemistry depicted in the table below:

| Structure | Name | Data[a] |
|---|---|---|
| (structure: cyclohexyl with vinyl, OH, CO₂t-Bu, methyls) | tert-Butyl 1-((1R*,2R*,6R*)-1-hydroxy-2,6-dimethyl-2-ethenylcyclohexyl) acetate | IR (neat) 3443 (broad), 2977, 2933, 1699, 1149 cm$^{-1}$; $^1$H NMR (300 MHz, CDCl$_3$) δ 6.28 (dd, J = 17.7, 11.0 Hz, 1H), 5.10-4.94 (m, 2H), 2.46 (d, J = 15.9 Hz, 1H), 2.17 (d, J = 15.9, 1.0 Hz, 1H), 2.08-1.87 (m, 1H), 1.81-1.68 (m, 1H), 1.43 (s, 9H), 1.31 (s, 1H), 1.03 (s, 3H), 0.84 (d, J = 6.6, 3H); $^{13}$C NMR (75 MHz, CDCl$_3$) δ 174.64 (q), 146.49 (d), 112.75 (q), 81.65 (q), 75.33 (q), 45.28 (q), 38.78 (t), 37.22 (d), 34.43 (t), 30.53 (t), 28.05 (s), 21.50 (t), 17.91 (s), 16.74 (s); GC-EIMS m/z (% rel. abundance) 212 (14), 194 (42), 96 (100) |
| (structure: cyclohexyl with vinyl, OAc, CO₂t-Bu, methyls) | tert-Butyl 1-((1R*,2R*,6R*)-1-acetoxy-2,6-dimethyl-2-ethenylcyclohexyl) acetate | IR (neat) 2976, 2935, 1730, 1149 cm$^{-1}$; $^1$H NMR (300 MHz, CDCl$_3$) δ 6.12 (dd, J = 17.6, 11.0 Hz, 1H), 5.02 (ddd, J = 17.8, 11.2, 1.6 Hz, 2H), 3.32 (d, J = 15.9 Hz, 1H), 3.17 (d, J = 15.9 Hz, 1H), 2.46-2.31 (m, 1H), 2.06 (s, 3H), 1.90 (m, 1H), 1.57-1.45 (m, 1H), 1.41 (s, 9H), 1.21-1.12 (m, 1H), 1.11 (s, 3H), 1.01 (d, J = 6.8 Hz, 3H); $^{13}$C NMR (75 MHz, CDCl$_3$) δ 170.55 (q), 169.94 (q), 145.02 (d), 112.40 (t), 89.06 (q), 80.17 (q), 45.68 (q), 37.51 (t), 35.88 (d), 35.00 (t), 30.31 (t), 28.04 (s), 22.62 (s), 20.97 (s), 20.45 (t), 17.94 (s). |

25. The compound in the table below, said compound having the relative stereochemistry depicted in the table below:

| Structure | Name | Data[a] |
|---|---|---|
| (structure: hexahydrobenzofuranone with ethyl and dimethyl substituents) | (3aS*,4S*,7aS*)-4,7a-Dimethyl-4-ethylhexahydrobenzofuran-2(3H)-one | IR (neat) 2939, 2871, 1770, 1028, 954, 928 cm$^{-1}$, $^1$H NMR (300 MHz, CDCl$_3$) δ 2.49 (dd, J = 16.3, 14.9 Hz, 1H), 2.31 (dd, J = 16.3, 6.5 Hz, 1H), 2.15-1.90 (m, 2H), 1.85-1.69 (m, 2H), 1.68-1.40 (m, 3H), 1.36 (s, 3H), 1.33-1.24 (m, 1H), 1.19-0.97 (m, 1H), 0.91 (s, 3H), 0.85 (t, J = 7.5 Hz, 3H), $^{13}$C NMR (75 MHz, CDCl$_3$) δ 176.62 (s), 86.57 (s), 56.81 (d), 37.68 (t), 36.36 (t), 35.68 (s), 29.40 (t), 27.64 (q), 24.44 (t), 21.08 (q), 20.53 (t), 9.05 (q), GC-EIMS m/z (% rel. abundance) 181 (70), 167 (37), 153 (73), 139 (25), 81 (93), 55 (100). |

26. The compound in the table below which may be used to make analogs of (±)-epianastrephin (1) and (±)-anastrephin (2), said compound having the relative stereochemistry depicted in the table below:

| Structure | Name | Data[a] |
|---|---|---|
| 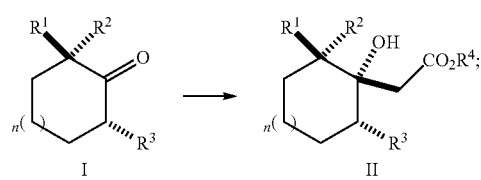 | tert-Butyl 1-((1R*,6R*)-1-acetoxy-2,2,6-trimethylcyclohexyl) acetate | IR (neat) 2976, 2932, 1729, 1148 cm⁻¹; ¹H NMR (300 MHz, CDCl₃) δ 3.34 (d, J = 15.8 Hz, 1H), 3.21 (d, J = 15.8 Hz, 1H), 2.42-2.24 (m, 1H), 2.05 (s, 3H), 1.78-1.63 (m, 1H), 1.55-1.39 (m, partially obscured by singlet at 1.42 ppm, 4H), 1.42 (s, 9H), 1.18-1.05 (m, 1H), 1.03 (d, partially obscured by singlets at 1.00 ppm, J = 6.6 Hz, 3H), 1.00 (s, 6H); ¹³C NMR (75 MHz, CDCl₃) δ 170.78 (s), 170.28 (s), 90.32 (s), 80.18 (s), 40.52 (s), 37.81 (t), 37.03 (t), 35.75 (d), 30.63 (t), 28.01 (q), 27.08 (q), 24.26 (q), 22.64 (q), 21.15 (t), 18.15 (q). |

27. The process according to claim 1, wherein:
$R^1$ is ethenyl or methyl,
$R^2$ is ethenyl or methyl,
$R^1$ and $R^2$ are not the same,
$R^3$ is methyl,
$R^4$ is methyl, ethyl, propyl, t-butyl, and
n is 1 to form a 6-membered ring.

28. A process of making trans-fused γ-lactones of the Formula (IV)

(IV)

wherein:
$R^1$ is ethenyl or methyl,
$R^2$ is ethenyl or methyl,
$R^1$ and $R^2$ are not the same,
$R^3$ is methyl,
$R^4$ is methyl, ethyl, propyl, t-butyl, and
n is 1 to form a 6-membered ring,
said process comprising:
(a) reacting the cyclic ketone of Formula (I) with an organometallic reagent $MCH_2CO_2R^4$ where M is Li, Na, K, or MgX, where X is Cl, Br or I, where $R^4$ is $C_{1-4}$ alkyl, in a solvent to form the alcohol of Formula (II)

(b) reacting the alcohol of Formula (II) with an acylating agent, or a chloroformate in the presence of a catalyst or a base in a solvent, or an acyl transfer reagent in the presence of an acid catalyst and organic catalyst in a solvent, to provide a compound of Formula (III) where $R^5$ is $-C(O)C_{1-6}$ alkyl or $-C(O)OC_{1-6}$ alkyl

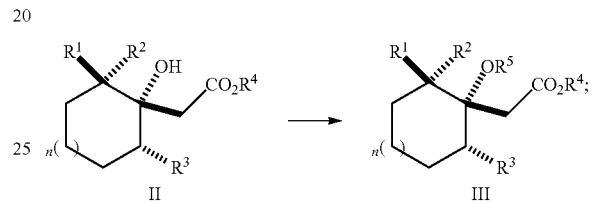

(c) cyclizing the compound of Formula (III) with an organic acid or a Lewis acid in a solvent to form the trans-fused γ-lactone of Formula (IV)

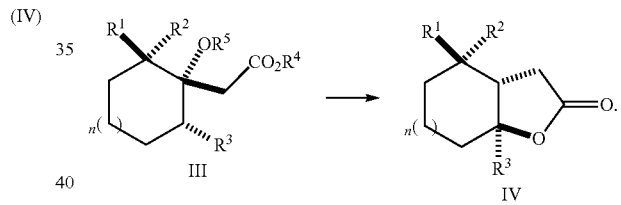

29. The process according to claim 28, wherein the solvent of step (a) is selected from the group consisting of THF, Et₂O, MTBE, DME or dioxane.

30. The process according to claim 28, wherein the organometallic reagent ($MCH_2CO_2R^4$) of step (a) is generated from (1) the corresponding neutral acetate precursor with a base selected from the group consisting of LDA or LiHMDS, NaHMDS, KHMDS, sodium hydride, potassium hydride, or from (2) the (Grignard reagent generated from the corresponding α-halo ester $XCH_2CO_2R^4$ where X is Cl, Br or I, and isopropyl magnesium bromide or magnesium.

31. The process according to claim 28, wherein the solvent of step (b) is selected from the group consisting of DCM, acetonitrile or nitromethane.

32. The process according to claim 28, wherein the catalyst of step (b) is selected from the group consisting of indium (III) chloride, LiOTf or NBS.

33. The process according to claim 28, wherein the organic base of step (b) is selected from the group consisting of Et₃N or Hunig's base.

34. The process according to claim 28, wherein the acyl transfer reagent of step (b) is selected from the group consisting of isopropenyl acetate, vinyl acetate or methyl vinyl acetate.

35. The process according to claim 28, wherein the acid catalyst of step (b) is selected from the group consisting of p-TsOH.H₂O or methane sulfonic acid.

36. The process according to claim 28, wherein the acyl transfer organic catalyst of step (b) is an oxime.

37. The process according to claim 28, wherein the organic acid of step (c) is selected from the group consisting of p-TsOH.H₂O or MeSO₃H, and a Lewis acid complex of step (c) is selected from the group consisting of BX₃.L, GaX₃.L or AlX₃ where X is F, Cl or Br, and where L is Et₂O or acetonitrile or dimethyl sulfide.

38. The process according to claim 28, wherein a so f step (c) is selected from the group consisting of acetonitrile or nitromethane.

39. The process according to claim 28 wherein said trans-fused γ-lactone of Formula (IV)

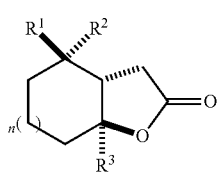

is (±)-epianastrephin (2),
wherein:
R¹ is ethenyl,
R² is methyl,
R³ is methyl, and
n is 1 to form a 6-membered ring,
said process comprising:
(a) reacting ketone 9 with a base followed by zinc chloride and acetaldehyde in a solvent to form alcohol 10

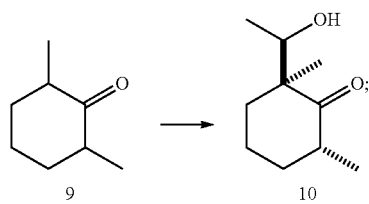

(b) reacting alcohol 10 with a dehydrating agent a solvent to form the vinyl ketone 11, or reacting alcohol 10 with a sulfonyl chloride followed by elimination with a base to form the vinyl ketone 11

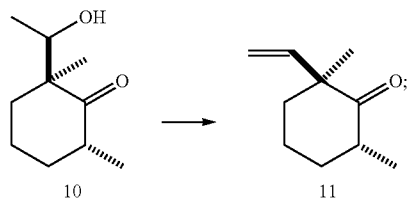

(c) reacting ketone 11 with an organometallic reagent MCH₂CO₂R₄ where M is Li, Na, K or MgX, where X is Cl, Br or I, where R⁴ is t-butyl in a solvent to form alcohols 12A and 12B

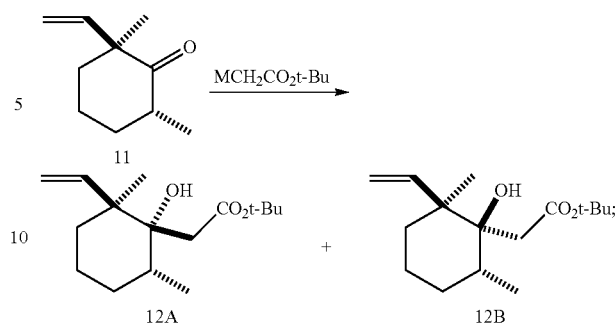

(d) reacting alcohol 12A with an acylating agent in the presence of an acid catalyst in a solvent to provide the acylated alcohol 13

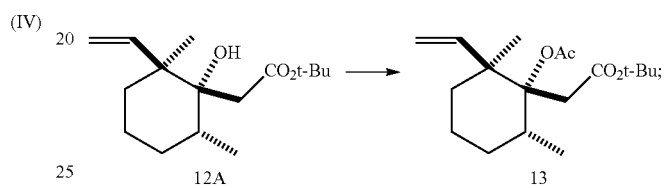

(e) cyclizing compound 13 with a Lewis acid complex in a solvent to form the trans-fused γ-lactone, (±)-epianastrephin (1)

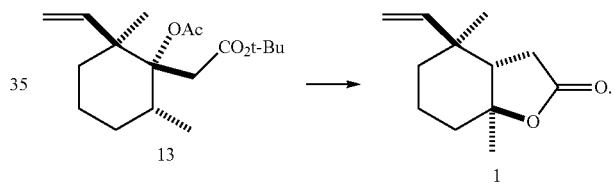

40. The process according to claim 39, wherein the dehydrating agent of step (b) is selected from the group consisting of Martin's sulfurane, Burgess's reagent, P₂O₅ or SOCl₂.

41. The process according to claim 28 wherein said trans-fused γ-lactone of Formula (IV)

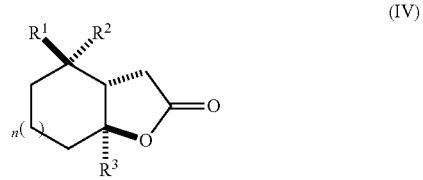

is (±)-anastrephin (2),
wherein:
R¹ is methyl,
R² is ethenyl,
R³ is methyl, and
n is 1 to form a 6-membered ring,
said process comprising:
(a) reacting ketone 9 with a silyl chloride, a base and sodium iodine in a solvent to form the silyl enol ether 14; or reacting ketone 9 with a base and a silyl chloride in a solvent to form the silyl enol ether 14

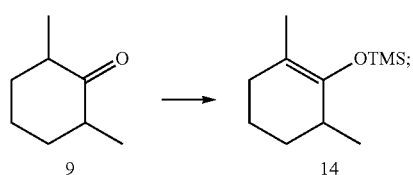

(b) reacting silyl enol ether 14 with TMSA in the presence of a Lewis acid in a solvent followed by the addition of THF and an acid to form the ketone 15

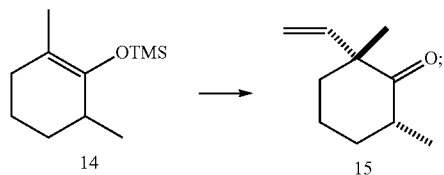

(c) reacting ketone 15 with an organometallic reagent MCH$_2$CO$_2$R$^4$ where M is Li, Na, K or MgX, where X is Cl, Br or I, where R$^4$ is t-butyl in a solvent to form alcohols 16A and 16B

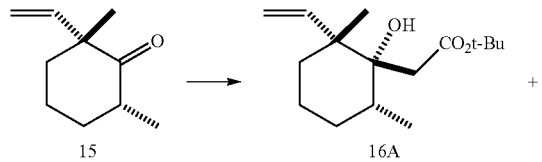

-continued (d) reacting alcohol 16A with an acylating agent in the presence of an acid catalyst and cyclohexanone oxime in a solvent to provide acylated alcohol 17

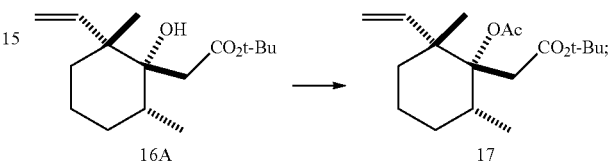

(e) cyclizing compound 17 with a Lewis acid or Lewis acid complex in a solvent to the trans-fused γ-lactone, (±)-anastrephin (2)

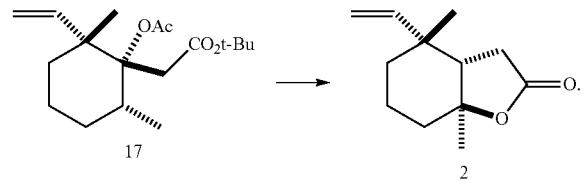

* * * * *